US005654308A

United States Patent [19]
Sugimoto et al.

[11] Patent Number: 5,654,308
[45] Date of Patent: Aug. 5, 1997

[54] BICYCLIC AMIDE DERIVATIVES, COMPOSITIONS AND METHODS OF TREATMENT

[75] Inventors: Hachiro Sugimoto; Masahiro Yonaga; Norio Karibe; Youichi Iimura; Satoshi Nagato; Atsushi Sasaki; Yoshiharu Yamanishi, all of Ibaraki, Japan; Hiroo Ogura, Bethesda, Md.; Takashi Kosasa; Kumi Uchikoshi, both of Ibaraki, Japan; Kiyomi Yamatsu, Kanagawa, Japan

[73] Assignee: Eisai Co., Ltd., Tokyo, Japan

[21] Appl. No.: 449,738

[22] Filed: May 25, 1995

Related U.S. Application Data

[62] Division of Ser. No. 165,490, Dec. 13, 1993, Pat. No. 5,504,088, which is a division of Ser. No. 715,754, Jun. 14, 1991, Pat. No. 5,292,735.

[30] Foreign Application Priority Data

Jun. 15, 1990  [JP]  Japan ........................ 2-157134

[51] Int. Cl.$^6$ ................ A61K 31/505; C07D 471/04
[52] U.S. Cl. ................................ 514/258; 544/279
[58] Field of Search ........................ 544/279; 514/258

[56] References Cited

U.S. PATENT DOCUMENTS

| | | | |
|---|---|---|---|
| 3,494,932 | 2/1970 | Brabander | 548/314.7 |
| 4,066,772 | 1/1978 | Van den Berk et al. | 424/267 |
| 4,073,911 | 2/1978 | Heubner | 424/267 |
| 4,137,318 | 1/1979 | Eberlein et al. | 424/258 |
| 4,174,443 | 11/1979 | Dalton | 544/86 |
| 4,344,948 | 8/1982 | Takai et al. | 424/251 |
| 4,420,615 | 12/1983 | Bolhofer et al. | 544/279 |
| 4,446,141 | 5/1984 | Nakamizo et al. | 424/267 |
| 4,490,369 | 12/1984 | Reiffen et al. | 424/244 |
| 4,505,911 | 3/1985 | Dolak et al. | 514/229 |
| 4,604,388 | 8/1986 | Leonard et al. | 514/211 |
| 4,737,495 | 4/1988 | Bomhard et al. | 514/213 |
| 4,849,431 | 7/1989 | Sugimoto et al. | 514/331 |
| 4,871,735 | 10/1989 | Heider et al. | 514/213 |
| 4,910,302 | 3/1990 | Abou-Gharbia et al. | 540/486 |
| 4,912,115 | 3/1990 | Bomhard et al. | 514/309 |
| 4,950,648 | 8/1990 | Raddatz et al. | 514/254 |
| 5,034,401 | 7/1991 | Frost et al. | 514/323 |
| 5,556,860 | 9/1996 | Muraoka et al. | 514/258 |

FOREIGN PATENT DOCUMENTS

| | | |
|---|---|---|
| 0004358 | 10/1979 | European Pat. Off. . |
| 0004793 | 10/1979 | European Pat. Off. . |
| 0013071 | 7/1980 | European Pat. Off. . |
| 0015138 | 9/1980 | European Pat. Off. . |
| 0029707 | 3/1981 | European Pat. Off. . |
| 0026749 | 4/1981 | European Pat. Off. . |
| 0047990 | 3/1982 | European Pat. Off. . |
| 0048218 | 3/1982 | European Pat. Off. . |
| 0049173 | 4/1982 | European Pat. Off. . |
| 0058055 | 8/1982 | European Pat. Off. . |
| 0065229 | 11/1982 | European Pat. Off. . |
| 0068331 | 1/1983 | European Pat. Off. . |
| 0091511 | 10/1983 | European Pat. Off. . |
| 0107930 | 5/1984 | European Pat. Off. . |
| 0111397 | 6/1984 | European Pat. Off. . |
| 0138198 | 4/1985 | European Pat. Off. . |
| 0170213 | 2/1986 | European Pat. Off. . |
| 0204349 | 12/1986 | European Pat. Off. . |
| 0229391 | 7/1987 | European Pat. Off. . |
| 0259793 | 3/1988 | European Pat. Off. . |
| 0269968 | 6/1988 | European Pat. Off. . |
| 296560 | 12/1988 | European Pat. Off. . |
| 0312283 | 4/1989 | European Pat. Off. . |
| 0326106 | 8/1989 | European Pat. Off. . |
| 0344577 | 12/1989 | European Pat. Off. . |
| 0351282 | 1/1990 | European Pat. Off. . |
| 0304330 | 12/1990 | European Pat. Off. . |
| 0441517 | 8/1991 | European Pat. Off. . |
| 0452204 | 10/1991 | European Pat. Off. . |
| 2639718 | 3/1978 | Germany . |
| 2924064 | 12/1980 | Germany . |
| 53-44574 | 4/1978 | Japan . |
| 55-024155 | 2/1980 | Japan . |
| 55-076872 | 6/1980 | Japan . |
| 56-142280 | 11/1981 | Japan . |
| 2193992 | 7/1990 | Japan . |
| 32155 | 1/1991 | Japan . |
| 8000024 | 1/1980 | WIPO . |
| 8101554 | 11/1981 | WIPO . |
| 9106297 | 5/1991 | WIPO . |
| 9112252 | 8/1991 | WIPO . |

OTHER PUBLICATIONS

Drug Evaluations, 6th Ed. (1986), Amer. Medical Assn. (pp. 160–162).
Cecil Textbook of Medicine, 19th Ed. (1992), Wyngarden, M.D., editor (pp. 2075–2079).

(List continued on next page.)

Primary Examiner—Philip I. Datlow
Attorney, Agent, or Firm—Birch, Stewart, Kolasch & Birch

[57] ABSTRACT

The cyclic amide derivative is defined by the formula (I) or a salt thereof: $R^1$—$(CH_2)n$-Z in which $R^1$ is a group derived from a cyclic amide compound, substituted or unsubstituted, n is zero or an integer of 1 to 10 and Z is $$\text{(1)} \quad \diagup\!\!\!\bigcirc\!\!\!\diagdown N\text{---}(CH_2)_m\text{---}R^2 \quad \text{or}$$

$$\text{(2)} \quad \begin{array}{c} R^3 \\ | \\ -N\text{---}(CH_2)_p\text{---}R^4 \end{array}$$

$R^2$ being an aryl, a substituted aryl, a cycloalkyl or a heterocyclic group, m being an integer of 1 to 6, $R^3$ being hydrogen or a lower alkyl, $R^4$ being an aryl or a substituted aryl, a cycloalkyl or a heterocyclic group, p being an integer of 1 to 6, provided that the cyclic amide compound is quinazoline-on or quinazoline-dion, $R^2$ and $R^4$ are neither aryl nor substituted aryl. The cyclic amide compound is pharmacologically effective to prevent and treat diseases due to insufficiency of the central choline functions.

17 Claims, No Drawings

OTHER PUBLICATIONS

R.A. Glennon et al., J.Med.Chem., vol. 32, 1989 pp. 1921–1926.

Abstracts of Japan, vol. 15, No. 104(C–814) (4632), 1991 & JP–A/32155.

T. Takeda et al., Chem.Pharm.Bull., vol. 35, No. 9, 1987 (pp. 3558–3567).

M. Niitsu et al., Chem.Pharm.Bull., vol. 34, No. 3, 1986 (pp. 1032–1038).

Helvetica Chimica Acta, vol. 64, No. 40, Fasc. 2, 1981 (pp. 399–406).

R. Granados et al., J.Heterocyclic Chem., vol. 20, No. 5, 1983 (pp. 1271–1275).

Abstracts of Japan, vol. 14, No. 435 (C–760) (4378, 1990) & JP–A 2169569.

Stamm et al., Chemical Abstract, vol. 61, No. 12012d (1964).

Patent Abstracts of Japan, vol. 15, No. 92, JP 2–306951 (1990).

Patent Abstracts of Japan, vol. 8, No. 205, JP 59–95265 (1984).

Patent Abstracts of Japan, vol. 14, No. 470, JP 2–193992 (1990).

Patent Abstracts of Japan, vol. 2, No. 85, JP 53–44574 (1978).

Patent Abstracts of Japan, vol. 6, No. 19, JP 56–142280 (1982).

Patent Abstracts of Japan, vol. 4, No. 54, JP 55–024155 (1980).

Patent Abstracts of Japan, vol. 4, No. 124, JP 55–076872 (1980).

BICYCLIC AMIDE DERIVATIVES, COMPOSITIONS AND METHODS OF TREATMENT

This application is a divisional of application Ser. No. 08/165,490, filed on Dec. 13, 1993 now U.S. Pat. No. 5,504,088, the entire contents of which are hereby incorporated by reference, and which is a divisional of Ser. No. 07/715,754/, filed on Jun. 14, 1991, now U.S. Pat. No. 5,292,735 also incorporated herein by reference.

The present invention relates to new cyclicamide derivatives such as piperidine compounds having excellent medicinal effects.

PRIOR ART

With a rapid increase in the population of the aged, the establishment of medical treatment for senile dementia such as Alzheimer's disease is eagerly demanded.

Although various treatments of senile dementia with medicines have been attempted, no medicine essentially effective for these diseases has been developed as of yet.

Various investigations are in progress for the purpose of developing therapeutic agents for these diseases. Particularly, the development of acetylcholine precursors and acetylcholine esterase inhibitors has been proposed, since Alzheimer's disease is associated with cerebral cholinergic hypofunction, and they are being tested. Typical examples of the anticholinergic esterase inhibitors include physostigmine and tetrahydroaminoacridine. However, they have defects in that their effects are yet insufficient and that they have adverse reactions. Thus there are no decisive therapeutic agents at present.

SUMMARY

Under these circumstances, the inventors have made intensive investigations of various compounds for a long period of time for the purpose of developing a medicine having high safety and a long-lasting effect.

As the result, the inventors have found that the purpose can be attained by using derivatives of the general formula (I) given below.

In particular, the compounds of the present invention represented by the structural formula (I) given below have features that they have potent, highly selective antiacetylcholine esterase activity in order to increase the quantity of acetylcholine in the brain, that they are effective for the therapy of models of the disturbance of memory, and that their effect lasts for a longer time and they have a higher safety than those of physostigmine frequently used in this field. The present invention is thus highly valuable.

The compounds of the present invention have been found on the basis of acetylcholine esterase inhibition and, therefore, they are effective for the treatment and prevention of various diseases due to insufficiency of the central choline functions, i.e. lack of acetylcholine as the neurotransmitter in vivo.

Typical examples of such diseases include dementias represented by Alzheimer's presbyophrenia. They include also Huntington's chorea, Pick's disease and tardive dyskinesia.

Therefore, objects of the present invention are to provide new piperidine derivatives usable as a medicine and particularly effective for the treatment and prevention of central nervous diseases, to provide a process for producing these new piperidine derivatives and to provide medicines comprising the piperidine derivative as the active ingredient.

The invention provides a cyclic amide derivative having the formula (I) or a pharmacologically acceptable salt thereof:

  (I)

in which $R^1$ is a group derived from a cyclic amide compound, substituted or unsubstituted, n is zero or an integer of 1 to 10 and Z is

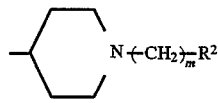  (1)

or

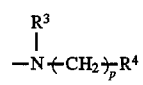  (2)

$R^2$ being an aryl, a substituted aryl, a cycloalkyl or a heterocyclic group, m being an integer of 1 to 6, $R^3$ being hydrogen or a lower alkyl, $R^4$ being an aryl or a substituted aryl, a cycloalkyl or a heterocyclic group, p being an integer of 1 to 6, provided that the cyclic amide compound is quinazoline-on or quinazoline-dion, $R^2$ and $R^4$ are neither aryl nor substituted aryl.

When Z is (1), it is preferable that $R^2$ is selected from phenyl, pyridyl, cyclopentyl and 1,3-dioxane-2-yl, n is 1 or 2, m is 1 or 2 and the cyclic amide compound for $R^1$ is selected from 2H-3,4-dihydro-1,3-benzoxazin-2-on, 2H-3, 4-dihydro-1,3-benzoxazin-2,4-dion, 1,2,3,4-tetrahydro-quinazolin-2,4-dion, 1,2,3,4-tetrahydro-quinazolin-2-on, 1,2,3,4-tetrahydro-pyrido (3.2-d)pyrimidine-2,4-dion, 1,2,3, 4-tetrahydro-pteridine-2,4-dion and 1,2,3,4-tetrahydro-pyrido(3.2-d)pyrimidine-2-on, It is preferable that $R^1$ is substituted with a lower alkyl or a lower alkoxy.

When Z is (2), it is preferable that $R^3$ is a lower alkyl and $R^4$ is selected from phenyl, pyridyl, cyclopentyl and 1,3-dioxane-2-yl.

In the formula (I), the following compounds are most preferable:
3-(2-(1-benzyl-4-piperidyl)ethyl)-5-methoxy-2H-3,4-dihydro-1,3-benzoxazine-2-one,
3-(2-(1-(4-pyridylmethyl)-4-piperidyl)ethyl)-2H-3,4-dihydro-1,3-benzoxazine-2-one,
3-(2-(1-(1,3-dioxoran-2-yl-methyl)-4-piperidine)ethyl)-6-methoxy-2H-3,4-dihydro-1,3-benzoxazine-2-on,
3-(2-(cyclopentylmethyl-4-piperidyl)ethyl)-2H-3,4-dihydro-1,3-benzoxazine-2,4-dione,
3-(2-(1-(1,3-dioxoran-2-yl-methyl)-4-piperidyl)ethyl)-2H-3,4-dihydro-1,3-benzoxazine-2,4-dione,
3-(2-(1-(1,3-dioxolan-2-yl-methyl)-4-piperidyl)ethyl)-5-methoxy-1,2,3,4-tetrahydro-quinazolin-2,4-dione
3-(2-(1-benzyl-4-piperidyl)ethyl)-6-methoxy-2H-3,4-dihydro-1,3-benzoxazine-2-one and
3-(2-(1-benzyl-4-piperidyl)ethyl)-6-methoxy-2H-3,4-dihydro-1,3-benzoxazine-2,4-dione.

The invention relates to the pharmacological use of the cyclic amide compound having the formula (I) and therefore provides a pharmaceutical composition comprising a pharmacologically effective amount of the cyclic amide derivative as defined above and a pharmacologically acceptable carrier and then a method for preventing and treating diseases due to insufficiency of the central choline functions by administering a pharmacologically effective amount of the derivative as defined above to a human patient suffering from the diseases.

The compound having the formula (I) includes that having the following formula (I'), called piperidine derivatives:

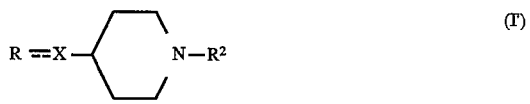

wherein $R^1$ represents a monovalent or divalent group derived from a substituted or unsubstituted cyclic amide compound, X represents a group of the formula: —(CH$_2$)$_n$— (wherein n is an integer of 1 to 6) or a group of the formula: =CH—(CH$_2$)$_p$—$_q$ (wherein p is an integer of 1 to 5 and q is an integer of 0 or 1), $R^2$ represents a group of the formula: —(CH$_2$)$_m$—A (wherein m is an integer of 1 to 6 and A is an aryl group which may be substituted, a cycloalkyl group, a pyridyl group, a 1,3-dioxolan-2-yl group, a furyl group, a thienyl group or a tetrahydrofuryl group), with the proviso that when the substituted or unsubstituted cyclic amide compound in the definition of $R^1$ is quinazolinone or quinazolinedione, A in the formula: (CH$_2$)$_m$—A in the definition of $R^2$ cannot be an aryl group, and symbol ------- represents a single or double bond, or pharmacologically acceptable salts thereof.

The monovalent groups derived from the cyclic amide compounds in the definition of the compound (I) of the present invention include 1,2,3,4-tetrahydroquinazolin-2-one, 1,2,3,4-tetrahydroquinazoline-2,4-dione, 2H-3,4-dihydro-1,3-benzoxazin-2-one, 2H-3,4-dihydro-1,3-benzoxazine-2,4-dione, 4-benzylpyrrolidin-2-one, 4-benzoylpyrrolidin-2-one, 1,2,3,4-tetrahydropteridin-2-one, 1,2,3,4-tetrahydropteridine-2,4-dione, 1,2,3,4-tetrahydropyrido[3,2-d]pyrimidin-2-one, 1,2,3,4-tetrahydropyrido[3,2-d]pyrimidine-2,4-dione, 8H-4,5,6,7-tetrahydroazepino[2,3-b]thiophen-7-one, 10-methyl-1H-2,3,4,5-tetrahydroazepino[2,3-b]indol-2-one, 1-methylene-3-oxoisoindoline, 7-methylenepyrrolidino[3,4-b]pyrazin-5-one, 4H-1,3-dimethylpyrazolo[5,4-c] [2]benzazepin-9-one, 7-hydroxy-7-methylpyrrolidino[3,4-b]pyrazin-5-one, 2H-3,4-dihydropyrido[2,3-e]-m-oxazin-2-one, 2H-3,4-dihydropyrido[2,3-e]-m-oxazine-2-thione, 5H-6,7,8,9-tetrahydro[3,2-b]azepin-6-one, 9H-5,6,7,8-tetrahydro[2,3-b]azepin-8-one and 2-benzoxazolinone, but they are not limited to those listed above and any of such compounds having a cyclic amide group in the structural formula can be used. The cyclic amides are those derived from monocyclic or condensed heterocyclic compounds. Preferable condensed heterocycles include heterocycles condensed with a benzene, thiophene, indole, pyrazine or pyrazole ring. The benzene ring may be substituted with one or two halogen atoms, preferably fluorine, chlorine or bromine, 1 to 3 lower alkoxy groups having 1 to 6 carbon atoms, preferably methoxy group, a lower alkyl group having 1 to 6 carbon atoms, or an amino, acetylamino or nitro group.

The term "lower alkyl groups" in the above definition include straight-chain and branched alkyl groups having 1 to 6 carbon atoms, such as methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among them, preferred are methyl, ethyl, propyl and isopropyl groups and the most desirable is a methyl group and ethyl group.

The term "lower alkoxy groups" refers to lower alkoxy groups having 1 to 6 carbon atoms derived from the above-described lower alkyl groups. Among them, the most desirable lower alkoxy groups include methoxy, ethoxy and n-propoxy groups.

Preferred examples of the groups derived from the cyclic amide compounds include the following compounds:

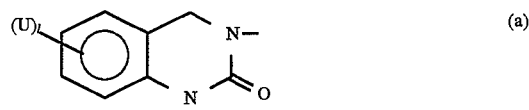

(a)

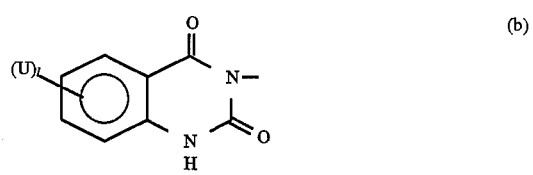

(b)

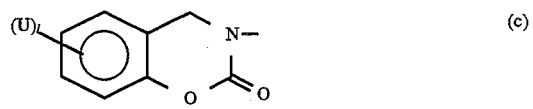

(c)

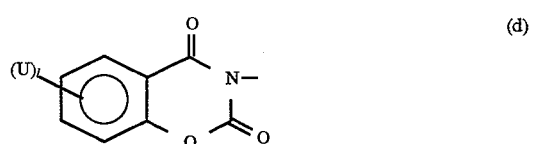

(d)

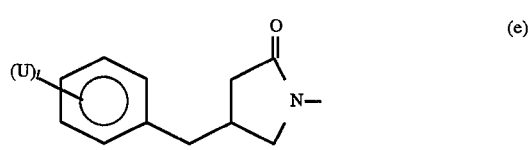

(e)

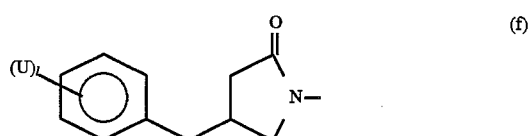

(f)

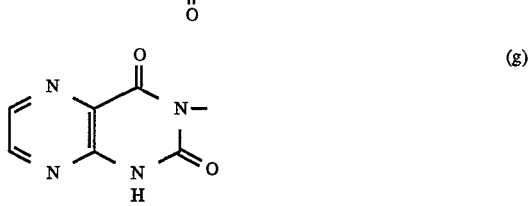

(g)

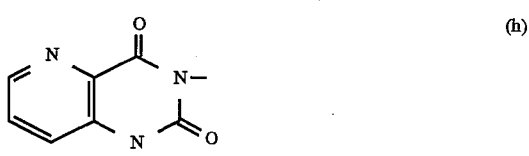

(h)

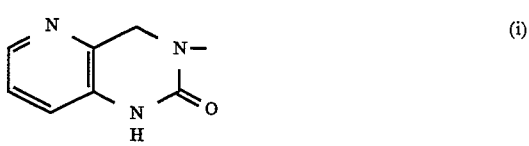

(i)

-continued

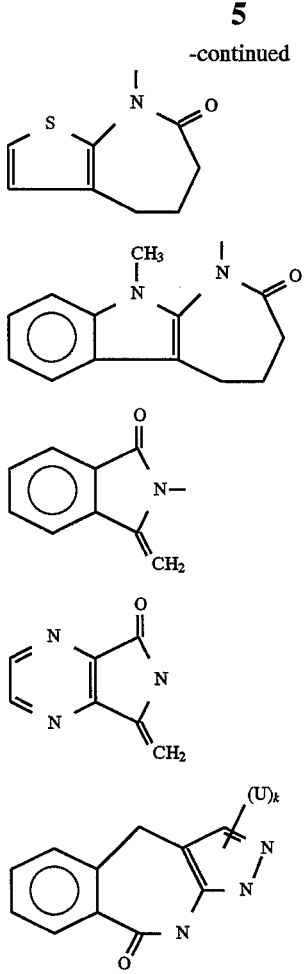

The group U is, independently of one another, hydrogen, a lower alkyl, a lower alkoxy, a halogen, an acyl, an amino or nitro. l is an integer of 1 to 4. k is 1 or 2. The formulae j and k has a 7-membered ring at the rightmost part and n has that at the center.

In the invention, n is preferably zero or an integer of 1 to 6 when Z is (1). n is more preferably 1 or 2 and most preferably 2. n is preferably an integer of 3 to 7 when Z is (2). n is more preferably 4 to 6 and most preferably 5.

Among (a) to (s) for $R^1$, (a), (b), (c), (d), (g), (h) and (i) are more preferable and (a), (b) and (d) are most preferable.

$R^1$ may have a substituent on the ring, preferably a lower alkyl such as methyl or a lower alkoxy such as methoxy. Methoxy on the benzene ring is most preferable for (a), (b) and (d) of $R^1$.

Preferable embodiments of $R^1$ include pyridyl such as 2-pyridyl, 3-pyridyl and 4-pyridyl, furyl such as 2-furyl and 3-furyl, a thienyl such as 2-thienyl and 3-thienyl, pyridinyl and a saturated hetero-monocyclic ring such as tetrahydrofuryl and 1,3-dioxolan-2-yl. Pyridyl and 1,3-dioxolan-2-yl are most preferable.

$R^2$ and $R^4$ preferably include a cycloalkyl such as cyclopropyl, cyclobutyl, cyclopentyl, cyclohexyl and cycloheptyl; an aryl such as phenyl and naphthyl; and a heterocyclic ring, 3- to 7-membered, including a nitrogen or one or two oxygen atoms, either monocyclic or a condensed ring, saturated or unsaturated. Phenyl, unsubstituted, is most preferable.

m and p are preferably 1 or 2 and most preferably 2.

The most important compound is defined by the formula (I) in which $R^1$ is (a), (b) or (d), n is 1 or 2, Z is (2), $R^2$ is phenyl, pyridyl or 1,3-dioxolan-2-yl and m is 1 or 2 (a), (b) and (d) may have a methoxy on the benzene ring.

The compounds having the formula (I) can be produced by analogous chemical processes for production. The processes are shown below for the compounds having the formula (I') and also apply to the compounds having the formula (I) by substituting Z for X. When Z is (2), the compounds (I) can be produced in the same way as here.

Production Process A:

When $R^1$ represents a group derived from a cyclic amide compound selected from among tetrahydroquinazolinedione, azatetrahydrobenzazepinone, benzylpiperidinone and benzoylpiperidinone, the compound can be produced by the following process:

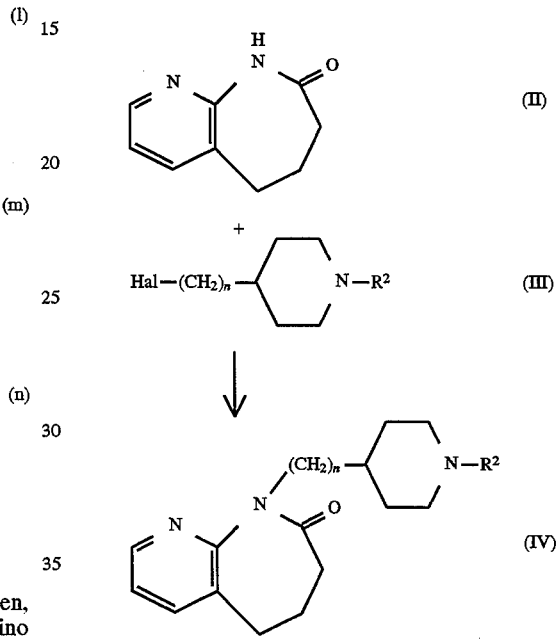

wherein n represents an integer of 1 to 6, $R^2$ is as defined above, and Hal represents a halogen atom.

Namely, 9-aza-1-benzazepin-2-one (II) is condensed with a compound of the general formula (III) in the presence of, for example, sodium hydride in, for example, dimethylformamide solvent in an ordinary manner to give an intended compound of the general formula (IV).

When $R^1$ is a monovalent group derived from a cyclic amide compound different from that described above, the starting compound

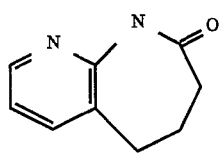

is replaced with tetrahydroquinazolinedione, benzylpiperidinone or benzoylpiperidinone, which is condensed with the compound of the general formula. (III) to give the intended compound readily.

Production Process B:

When $R^1$ represents a group derived from tetrahydroquinazolinedione and the compound can be produced by the following process:

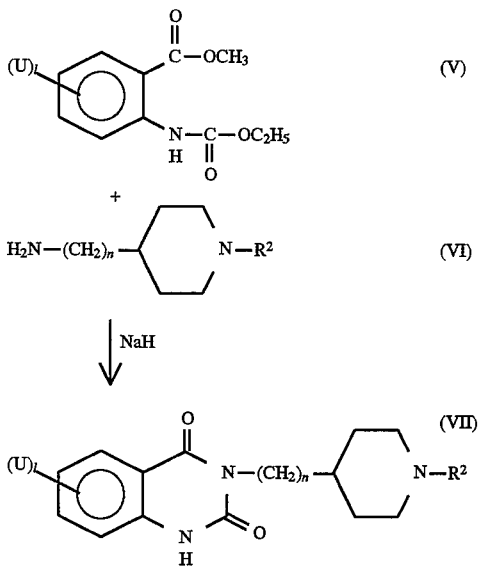

wherein U, l, n and R² are as defined above.

Namely, a diester of the general formula (V) is reacted with a piperidine derivative of the general formula (VI) under heating in a suitable solvent inert to the reaction or without any solvent to give a quinazolone compound (VII) which is one of the intended compounds.

Production process C:

When R¹ in the general formula (I) represents a group derived from tetrahydroquinazolinedione, tetrahydropteridinedione or tetrahydropyridinopyrimidinedione, the compound can be produced also by the following process:

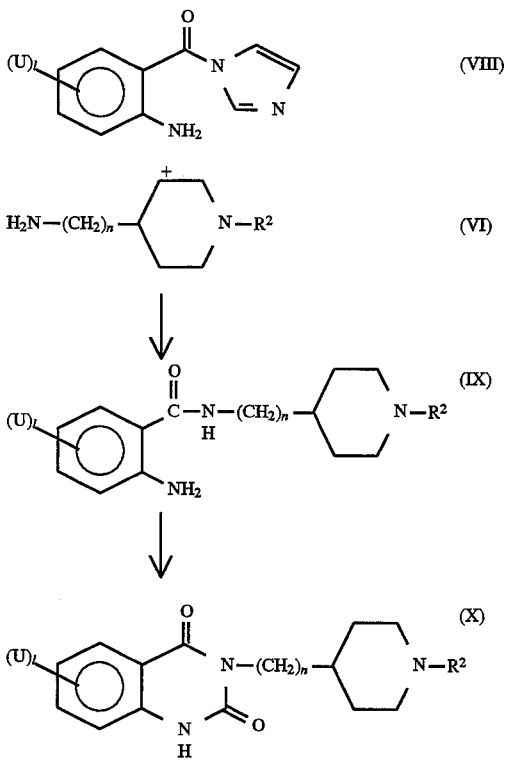

wherein U, l, n and R² are as defined above.

Namely, an N-acyl derivative of the general formula (VIII) is condensed with an amine of the general formula (VI) in a solvent such as tetrahydrofuran and the condensate is further reacted with 1,1-carbonyldiimidazole to give a compound (X) which is one of the intended compounds.

Production process D:

When R¹ in the general formula (I) represents a monovalent group derived from a substituted or unsubstituted tetrahydrobenzoxazinone, the compound can be produced also by the following process:

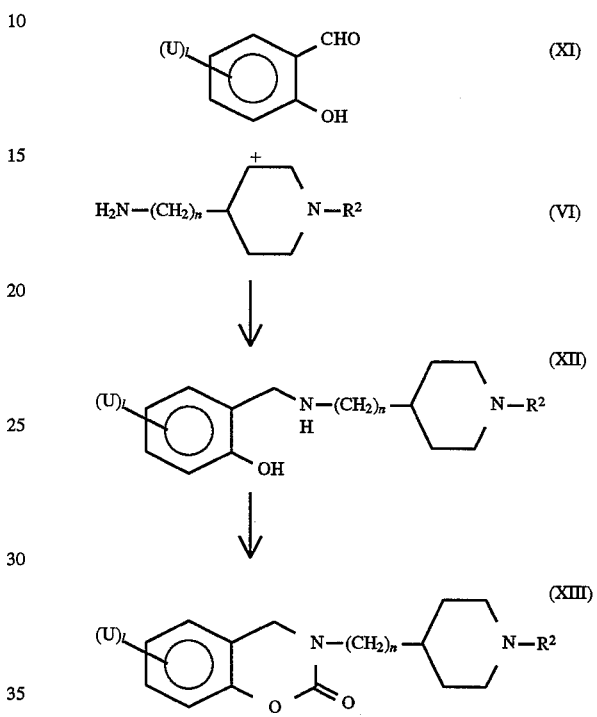

wherein U, l, n and R² are as defined above.

Namely, a salicylaldehyde derivative of the general formula (XI) is condensed with an amine of the general formula (VI) in a solvent such as methanol and the condensate is reduced with sodium borohydride to give a compound (XII). This compound is reacted with 1,1-carbonyldiimidazole in a solvent such as tetrahydrofuran to give a compound (XIII) which is one of the intended compounds.

Production process E:

When R¹ in the general formula (I) represents a group derived from a substituted or unsubstituted tetrahydrobenzoxazinedione, and R² represents a substituted or unsubstituted arylmethyl, furylmethyl or thienylmethyl group or the like,-the compound can be produced also by the following process:

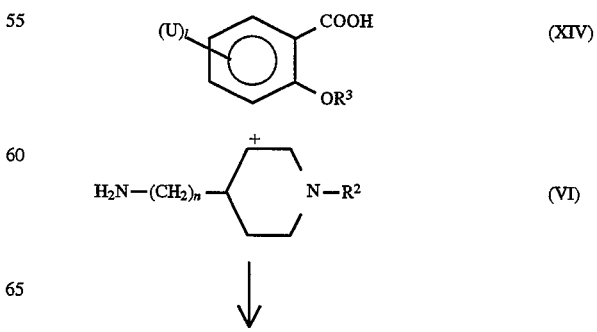

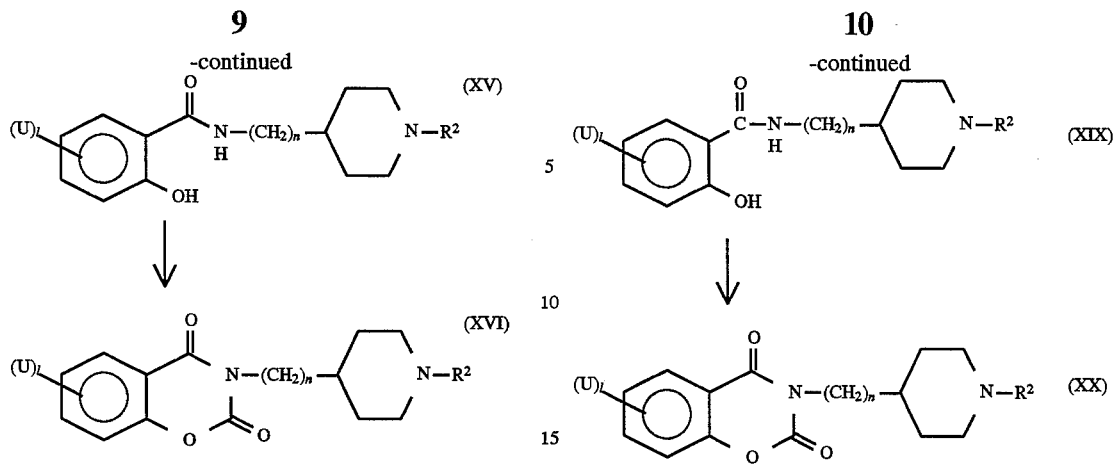

wherein U, l, n and R² are as defined above, and R³ represents a protective group such as a methoxymethyl or methoxyethoxymethyl group.

Namely, a salicylic acid derivative of the general formula (XIV) and an amine of the general formula (VI) are condensed with, for example, 1,1-carbonyldiimidazole in a solvent such as tetrahydrofuran, and the protective group is removed with an acid such as hydrochloric acid to form a compound (XV). This compound is reacted with 1,1-carbonyldiimidazole in a solvent such as tetrahydrofuran to give a compound (XVI) which is one of the intended compounds.

Production process F:

When R¹ in the general formula (I) represents a group derived from a substituted or unsubstituted tetrahydrobenzoxazinedione, and R² represents a cycloalkylmethyl, 1,3-dioxolan-2-ylmethyl or tetrahydrofurylmethyl group or the like, the compound can be produced also by the following process:

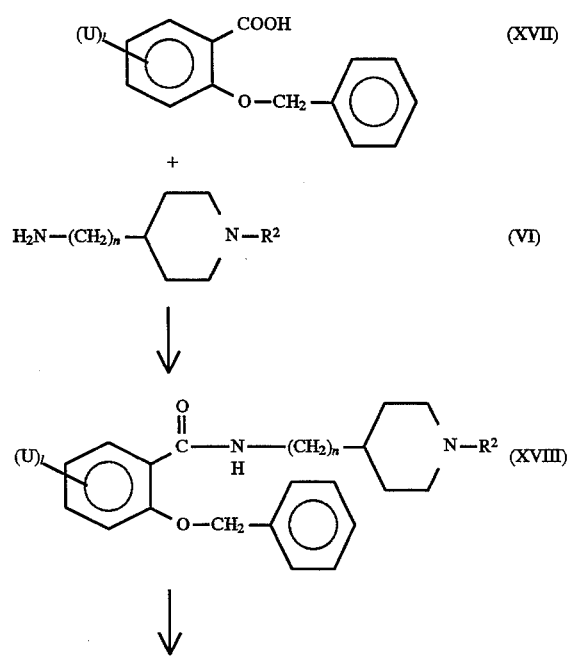

wherein U, l, n and R² are as defined above.

Namely, a salicylic acid derivative of the general formula (XVII) and an amine of the general formula (VI) are condensed with, for example, 1,1-carbonyldiimidazole in a solvent such as tetrahydrofuran to give a compound (XVIII) and the protective group is removed therefrom by catalytic reduction conducted in the presence of Pd—C or the like in a solvent such as methanol. This compound is reacted with 1,1-carbonyldiimidazole in a solvent such as tetrahydrofuran to give a compound (XIX) which is one of the intended compounds.

Production process G:

When R¹ in the general formula (I) represents a group derived from a substituted or unsubstituted tetrahydroquinazolinone or tetrahydropteridinone and the compound can be produced also by the following process:

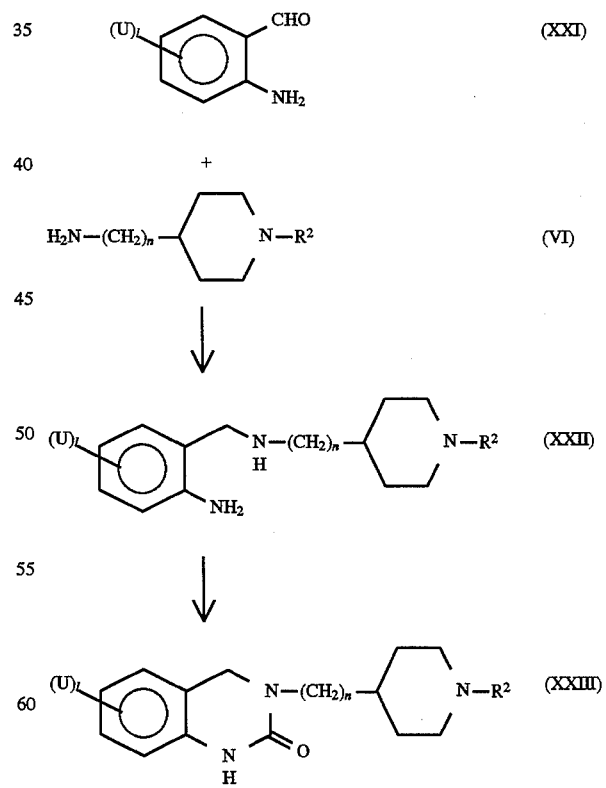

wherein U, l, n and R² are as defined above.

Namely, an aminobenzaldehyde derivative of the general formula (XXI) is condensed with an amine of the general formula (VI) in a solvent such as methanol and the condensate is reduced with sodium borohydride to give a compound (XXII), which is reacted with 1-carbonyldiimidazole in a solvent such as tetrahydrofuran to give a compound (XXIII) which is one of the intended compounds.

Production process H:

When $R^1$ in the general formula (I) represents a group derived from a substituted or unsubstituted tetrahydrobenzoxazin-2-one or tetrahydrobenzoxazine-2,4-dione and the compound can be produced also by the following process:

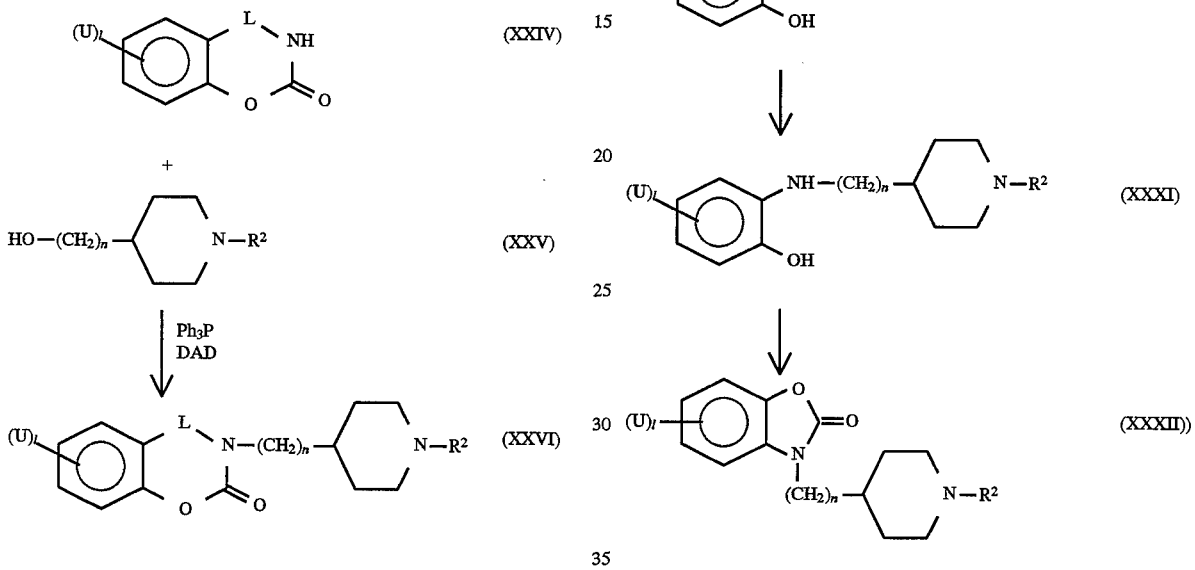

wherein U, l, n and $R^2$ are as defined above and L represents a carbonyl or methylene group.

Namely, a cyclic amide compound of the general formula (XXIV) is condensed with an alcohol of the general formula (XXV) in a solvent such as tetrahydrofuran in the presence of diethyl azodicarboxylate or diisopropyl azodicarboxylate and triphenylphosphine to give a compound (XXVI) which is one of the intended compounds.

Production process I:

When $R^1$ in the general formula (I) represents a group derived from a substituted or unsubstituted tetrahydrobenzoxazin-2-one or 2-benzoxazolinone and the compound can be produced also by the following process:

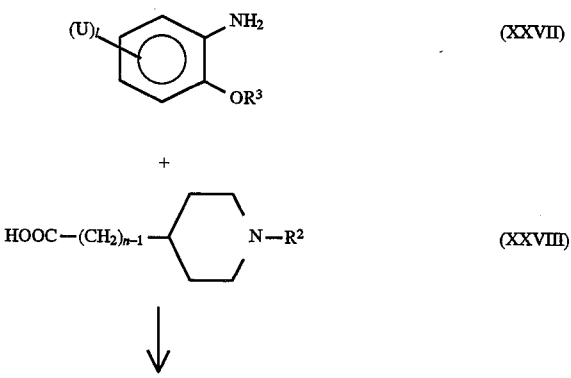

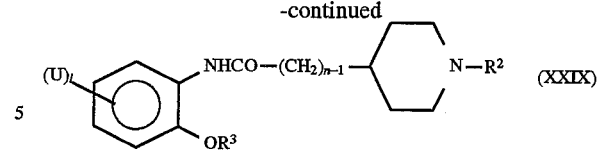

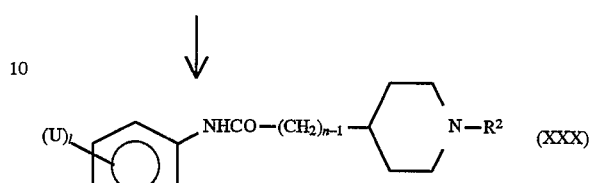

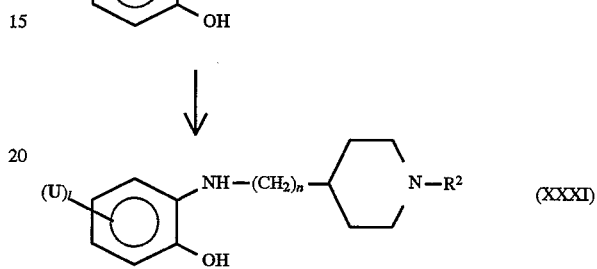

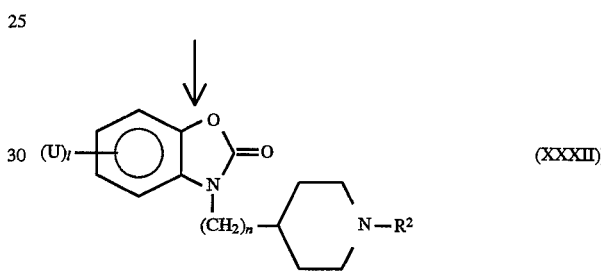

wherein U, l, n and $R^2$ are as defined above and represents a protective group such as a benzyl, methoxymethyl or methoxyethoxymethyl group.

Namely, an amine of the general formula (XXVII) is condensed with a carboxylic acid of the general formula (XXVIII) to give an amide compound (XXIV) and the protective group is removed therefrom to give a compound (XXX), which is reduced with lithium aluminum hydride in a solvent such as tetrahydrofuran to give an amine (XXXI). This compound is reacted with 1-carbonyldiimidazole in a solvent such as tetrahydrofuran or acetonitrile to give a compound (XXXII) which is one of the intended compounds.

The compounds of the formula (I) or acid addition salts thereof produced as described above are effective for the treatment of various senile dementias, particularly Alzheimer's disease.

The following results of pharmacological tests will illustrate the usefulness of the compounds of the general formula (I) and acid addition salts thereof.

Experimental Example 1

Acetylcholine esteraze inhibition effect in vitro:

The esterase activity was determined by using a mouse brain homogenate as the acetylcholine esterase source by the method of Ellmann et al[1].

Acetylthiocholine as the substrate, the sample and DTNB were added to the mouse brain homogenate and they were incubated. A yellow product formed by the reaction of the produced thiocholine with DTNB was determined on the basis of a change in absorbance at 412 nm to determine the acetylcholine esterase activity.

The acetylcholine esterase inhibiting activity of the sample was expressed in terms of 50% inhibiting concentration ($IC_{50}$), The results are given in Table 1.

1) Ellman, G. L., Courtney, K. D., Andres, V. and Featherstone, R. M., (1961)Piochem. Pharmacol., 7, 88–95.

TABLE 1

| Compound (Ex. No.) | AChE inhibiting activity $IC_{50}$ (nM) |
| --- | --- |
| 1 | 0.03 |
| 2 | 4.94 |
| 3 | 8.52 |
| 4 | 7.93 |
| 5 | 49.5 |
| 6 | 4.86 |
| 7 | 124.5 |
| 9 | 8.38 |
| 10 | 31.8 |
| 11 | 99.6 |
| 12 | 1.82 |
| 13 | 20.3 |
| 14 | 23.8 |
| 20 | 69.1 |
| 23 | 3.92 |
| 24 | 1.87 |
| 25 | 2.74 |
| 26 | 0.50 |
| 27 | 45.4 |
| 28 | 0.38 |
| 30 | 29.1 |
| 31 | 0.58 |
| 32 | 1.39 |
| 33 | 0.20 |
| 34 | 13.8 |
| 35 | 1.85 |
| 36 | 1.17 |
| 37 | 2.97 |
| 38 | 0.70 |
| 39 | 7.79 |
| 40 | 1024.6 |
| 41 | 4.64 |
| 42 | 3.92 |
| 43 | 2.96 |
| 44 | 5.04 |
| 46 | 11.4 |
| 52 | 64.9 |
| 53 | 0.18 |
| 54 | 0.34 |
| 60 | $5.6 \times 10^4$ |
| 61 | 0.79 |
| 62 | 10.4 |
| 64 | 9.11 |
| 65 | $3.4 \times 10^4$ |
| 66 | 288.1 |
| 68 | 219.6 |
| 71 | 137.3 |
| 74 | 27.7 |
| 75 | 20.8 |

It is apparent from the above-described pharmacological experimental examples that the piperidine derivatives of the present invention have potent acetylcholine esterase inhibiting effect.

The cyclic amide derivatives obtained by the present invention have such features that the structure thereof is quite different from that of ordinary acetylcholine esterase inhibitors, that they have a potent acetylcholine esterase inhibiting effect, that the difference between the intended effect and adverse effect thereof is quite large, that the effect lasts for a long time, that they are quite stable compounds having a high water solubility, which is advantageous from the viewpoint of formulation, that their utilization in vivo is high, that they are substantially free from the first pass effect and that they have a high migration rate into the brain.

Thus the object of the present invention is to provide new compounds effective for the treatment of various dementias and sequelae of cerebral blood vessel disorders, process for producing these compounds and a new medicine containing such a compound as the active ingredient.

The compounds of the present invention are effective for the treatment, prevention, remission, improvement, etc. of senile dementias; particularly cerebral blood vessel disorders due to Alzheimer's presbyophrenia, cerebral stroke (cerebral hemorrhage or cerebral infarction), arteriosclerosis and external wounds of the head; and inattentiveness, disturbances of speech, weakened volitions emotional disorders inability to fix, hallucination-delusion states and behavior changes owing to sequelae of cerebritis and cerebral palsy.

The compounds of the present invention having a potent, highly selective anticholine esterase inhibiting effect are useful as medicines having such an effect.

The compounds of the present invention are effective for the treatment of Alzheimer's presbyophrenia as well as Huntington's chorea, Pick's disease and tardive dyskinesia.

When the compounds of the present invention are used as a medicine for such a disease, they are given orally or parenterally. Usually, they are given by parenteral administration such as intravenous, subcutaneous or intramuscular injection or in the form of suppositories or sublingual tablets. The dose of the compounds is not particularly limited, since it varies depending on the symptoms; age, sex, body weight and sensitivity of the patient; medication; period and intervals of the administration, properties, composition and kind of the preparation; and kind of the active ingredient. Usually, however, they are given in an amount of about 0.1 to 300 mg, preferably about 1 to 100 mg, per day (1 to 4 times a day).

The compounds of the present invention are formulated into injections, suppositories, sublingual tablets, tablets or capsules by an ordinary method employed in the technical field of the formulation.

The injections are prepared by adding, if necessary, a pH adjustor, buffering agent, suspending agent, solubilizer, stabilizer, isotonizing agent and preservative to the active ingredient and they are formulated into the intravenous, subcutaneous or intramuscular injection. If necessary, they can be freeze-dried by any ordinary method.

Examples of the suspending agents include methylcellulose, Polysorbate 80, hydroxyethylcellulose, acacia, tragacanth powder, sodium carboxymethylcellulose and polyoxyethylene sorbitan monolaurate.

Examples of the solubilizers include polyoxyethylene-hardened castor oil, Polysorbate 80, nicotinamide, polyoxyethylene sorbitan monolaurate, macrogol and ethyl esters of castor oil fatty acids.

Examples of the stabilizers include sodium sulfite, sodium metasulfite and ethers. Examples of the preservatives include methyl p-hydroxybenzoate, ethyl p-hydroxybenzoate, sorbic acid, phenol, cresol and chlorocresol.

EXAMPLES

The following Examples will further illustrate the present invention, which by no means limit the technical range of the present invention.

Example 1

3-[2-(1-Benzyl-4-piperidyl)ethyl]-5-methoxy-2H-3,4-dihydro-1,3-benzoxazin-2-one hydrochloride

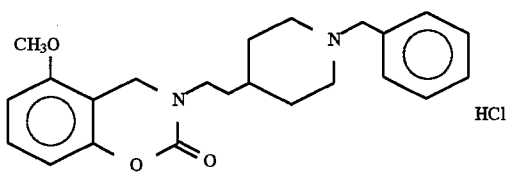

10 ml of methanol was added to 1.87 g of 1-benzyl-4-(2-aminoethyl)piperidine to give a solution and a solution of 0.53 g of 6-methoxysalicylaldehyde in 10 ml of methanol was added thereto. The mixture was stirred at room temperature for 30 min and then cooled with ice. Sodium borohydride was added thereto in small portions to conduct reduction. The solvent was distilled off and water was added to the residue. After extraction with ethyl acetate followed by drying over magnesium sulfate, the solvent was distilled off. An oily product thus obtained was dissolved in 50 ml of tetrahydrofuran and 2.77 g of N,N'-carbonyldiimidazole was added thereto. The mixture was heated under reflux for 1 h. The solvent was distilled off and an oily substance thus obtained was purified by silica gel column chromatography. The product was converted into its hydrochloride by an ordinary method to give 0.31 g of the intended compound in a colorless, amorphous form.

Melting point: amorphous

Molecular formula: $C_{23}H_{28}N_2O_3 \cdot HCl$

NMR (CDCl$_3$) δ: 1.20~2.12 (9H, m), 2.84 (2H, bd), 3.37~3.54 (4H, m), 3.80 (3H, s), 4.29 (2H, s), 6.54 (1H, q, J=2.1 Hz, 8.2 Hz), 7.04~7.18 (7H, m)

MS: (M+1$^+$)=381

Example 2

3-[2-(1-Benzyl-4-piperidyl)ethyl]-2H-3,4-dihydro-1,3-benzoxazin-2-one hydrochloride

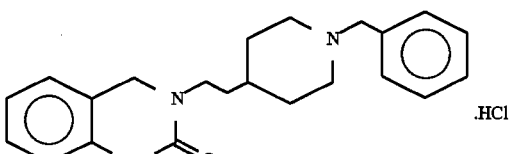

6 ml Of methanol was added to 0.954 g of 1-benzyl-4-(2-aminoethyl)piperidine to obtain a solution and a solution of 0.53 g of salicylaldehyde in 6 ml of methanol was added thereto. The mixture was stirred at room temperature for 30 min and then cooled with ice. Sodium borohydride was added thereto in small portions to conduct reduction. The solvent was distilled off and water was added to the residue. After extraction with ethyl acetate followed by drying over magnesium sulfate, the solvent was distilled off. An oily product thus obtained was dissolved in 15 ml of acetonitrile and 2.58 g of N,N'-carbonyldiimidazole was added thereto. The mixture was heated under reflux for 1 h. The solvent was distilled off and an oily substrate thus obtained was purified by silica gel column chromatography. The product was converted into its hydrochloride by an ordinary method to give 0.68 g of the intended compound in a colorless, amorphous form.

Melting point: 209.8° to 210° C.

Molecular formula: $C_{22}H_{26}N_2O_2 \cdot HCl$

NMR (CDCl$_3$) δ: 1.24~2.08 (9H, m), 2.83 (2H, bd), 3.45 (2H, s), 3.46 (2H, t, J=7.5 Hz), 4.38 (2H, s), 6.89~7.34 (9H, m)

MS: (M+1$^+$)=351

Example 3

3-[2-(1-Benzyl-4-piperidyl)ethyl]-2H-3,4-dihydro-1,3-benzoxazine-2,4-dione hydrochloride

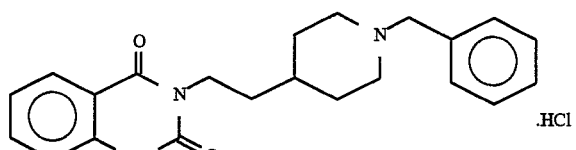

2.15 g of 4-[2-(2-hydroxybenzoylamino)ethyl]-1-benzylpiperidine was dissolved in 70 ml of tetrahydrofuran and 2.06 g of N,N'-carbonyldiimidazole was added thereto. The mixture was heated under reflux for 24 h. The solvent was distilled-off and an oily substance thus obtained was purified by silica gel column chromatography. The product was converted into its hydrochloride by an ordinary method to give 2.14.g of the intended compound in a colorless, amorphous form.

Melting point: 225.3° to 227.1° C. (decomp.)

Molecular formula: $C_{22}H_{24}N_2O_3 \cdot HCl$

NMR (CDCl$_3$) δ: 1.24~2.19 (9H, m), 2.86 (2H, bd), 3.46 (2H, s), 4.02 (2H, t, J=7.5 Hz), 7.14~7.36 (7H, m), 7.59 (1H, q, J=1.8 Hz, 8.0 Hz), 8.00 (1H, q, J=1.8 Hz, 8.0 Hz)

MS: (M+1$^{10}$)=365

Example 4

3-{2-[1-(4-Pyridylmethyl)-4-piperidyl]ethyl}-6-methoxy-2H-3,4-dihydro-1,3-benzoxazin-2-one dihydrochloride

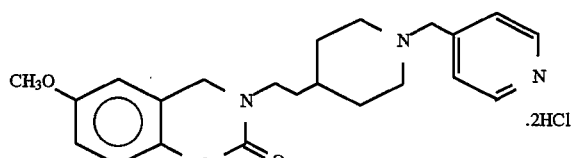

10 ml of methanol was added to 0.83 g of 1-(4-pyridylmethyl)-4-(2-aminoethyl)piperidine to give a solution and a solution of 0.63 g of 5-methoxysalicylaldehyde in 5 ml of methanol was added thereto. The mixture was stirred at room temperature for 30 min and then cooled with ice. Sodium borohydride was added thereto in small portions to conduct reduction. The solvent was distilled off and water was added to the residue. After extraction with ethyl acetate followed by drying over magnesium sulfate, the solvent was distilled off. An oily product thus obtained was dissolved in 20 ml of acetonitrile and 2.28 g of N,N'-carbonyldiimidazole was added thereto. The mixture was heated under reflux for 4 h. The solvent was distilled off and an oily substance thus obtained was purified by silica gel column chromatography. The product was converted into its hydrochloride by an ordinary method and recrystallized from methanol/ether to give 0.35 g of the intended compound in the form of colorless, needle-like crystals.

Melting point: 132.2° to 132.8° C. (decomp.)

Molecular formula: $C_{22}H_{27}N_3O_3 \cdot 2HCl$

NMR (CDCl$_3$) δ: 1.20~2.13 (9H, m), 2.82 (2H, bd), 3.46 (2H, s), 3.48 (2H, t, J=7.5 Hz), 3.75 (3H, s), 4.18 (2H, s), 6.58 (1H, dd, J=2.8 Hz, 8.5 Hz), 6.79 (1H, d, J=2.8 Hz), 6.92 (1H, d, J=8.5 Hz), 7.23 (2H, d, J=6.2 Hz), 8.48 (2H, d, J=6.2 Hz)

MS: (M+1$^+$)=382

Example 5

3-{2-[1-(1,3-Dioxolan-2-ylmethyl)}-4-piperidine] ethyl}-6-methoxy-2H-3,4-dihydro-1,3-benzoxazin-2-one hydrochloride

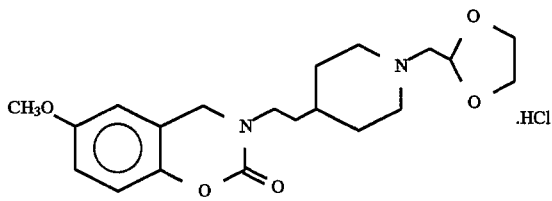

0.70 g of 5-methoxysalicylaldehyde was dissolved in 10 ml of methanol and a solution of 1.28 g of 1 -(1,3-dioxolan-2-ylmethyl)-4-(2-aminoethyl)piperidine in 10 ml of methanol was added thereto. The mixture was stirred at room temperature for 1 h and then sodium borohydride was added thereto under cooling with ice until yellow color disappeared. The reaction mixture was concentrated under reduced pressure and 150 ml of a saturated aqueous sodium hydrogen carbonate solution was added thereto. After extraction with 100 ml of methylene chloride twice followed by washing with 150 ml of an aqueous sodium chloride solution or brine and drying over magnesium sulfate, the product was concentrated under reduced pressure. An oily product thus obtained was dissolved in 100 ml of acetonitrile and 2.98 g of N,N'-carbonyldiimidazole was added thereto. The mixture was heated under reflux for 3 h and then left to cool to room temperature. After concentration under reduced pressure, 200 ml of ethyl acetate was added to the residue, which was washed with 200 ml of a saturated aqueous sodium hydrogen carbonate solution and then with 200 ml of a saturated aqueous sodium chloride solution. After drying over magnesium sulfate followed by concentration under reduced pressure, the residue was purified by silica gel column chromatography (methylene chloride:methanol= 100:1). A white solid thus obtained was recrystallized from ethyl acetate/hexane to give 1.30 g of white crystals. The product was converted into hydrochloride thereof to given 1.43 g (yield: 75%) of the intended compound in amorphous form.

Melting point: amorphous

Molecular formula: $C_{22}H_{28}N_2O_5 \cdot HCl$

NMR (CDCl$_3$) δ: 1.30~1.41 (3H, m), 1.60 (2H, dd), 1.72 (2H, d), 2.06 (2H, t), 2.56 (2H, d), 2.98 (2H, d), 3.49 (2H, dd), 3.78 (3H, s), 3.82~4.00 (4H, m), 4.41 (2H, s), 5.00 (1H, t), 6.60 (1H, d), 6.79 (1H, dd), 6.95 (1H, d)

MS: (M+1$^+$)=377

Example 6

3-[2-(1-Cyclopentylmethyl-4-piperidyl)-6-methoxyethyl]-2H-3,4-dihydro-1,3-benzoxazine-2,4-dione hydrochloride

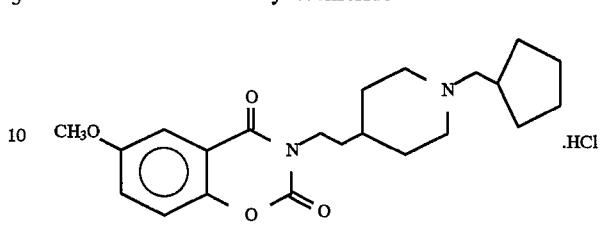

0.91 g of 4-[2-(2-benzyloxy-5-methoxybenzoylamino) ethyl]-1-cyclopentylmethylpiperidine was dissolved in 50 ml of methanol and 0.07 g of 10% Pd—C was added thereto. The mixture was stirred at room temperature in a hydrogen atmosphere for 1 h. The used Pd—C was removed by filtration and the solvent was distilled off to give a light yellow oily substance. 30 ml of tetrahydrofuran was added thereto to give a solution and 0.65 g of N,N'-carbonyldiimidazole was added thereto. The mixture was heated under reflux for 13 h. The solvent was distilled off and an oily substance thus obtained was purified by silica gel column chromatography. It was converted into hydrochloride thereof in an ordinary manner and recrystallized from methanol/ether to give 0.39 g of the intended compound in the form of colorless needle-like crystals.

Melting point: 213.5° to 214.1° C.

Molecular formula: $C_{22}H_{30}N_2O_4 \cdot HCl$

NMR (CDCl$_3$) δ: 1.17~1.21 (2H, m), 1.36~1.39 (3H, m), 1.50~1.68 (6H, m), 1.74~1.79 (4H, m), 1.97 (2H, t, J=10.8 Hz), 2.08 (1H, septet, J=7.6 Hz), 2.31 (1H, d, J=7.2 Hz), 2.97 (2H, bd), 3.87 (3H, s), 4.06 (2H, m), 7.19 (1H, d, J=9.2 Hz), 7.25 (1H, dd, J=3.2 Hz, 9.2 Hz), 7.45 (1H, d, J=3.2 Hz)

MS: (M+1$^+$)=387

Example 7

3-{2-[1-(1,3-Dioxolan-2-ylmethyl)-4-piperidyl] ethyl}-6-methoxy-2H-3,4-dihydro-1,3-benzoxazine-2,4-dione hydrochloride

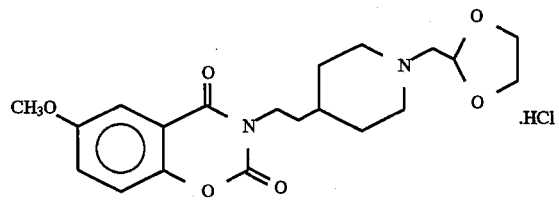

0.99 g of 4-[2-(2-benzyloxy-5-methoxybenzoylamino) ethyl]-1-(1,3-dioxolan-2-ylmethyl)piperidine was dissolved in 30 ml of methanol and 0.11 g of 10% Pd—C was added thereto. The mixture was stirred at room temperature in a hydrogen atmosphere for 2 h. The used Pd—C was removed by filtration and the solvent was distilled off to give 0.82 g of a light yellow oily substance. 30 ml of tetrahydrofuran was added thereto to give a solution and 0.71 g of N,N'-carbonyldiimidazole was added thereto. The mixture was heated under reflux for 20 h. The solvent was distilled off and an oily substance thus obtained was purified by silica gel column chromatography. It was converted into hydrochloride thereof in an ordinary manner and recrystallized from methanol/ether to give 0.85 g of the intended compound as colorless needles.

Melting point: 155.3° to 156.8° C.

Molecular formula: $C_{20}H_{26}N_2O_6 \cdot HCl$

NMR(CDCl$_3$) δ: 1.35~1.43 (3H, m), 1.64 (2H, bq), 1.76 (2H, bd), 2.08 (2H, t, J=11.0 Hz), 2.56 (2H, d, J=4.4 Hz), 300 (2H, bd), 3.87 (3H, s), 3.82~3.90 (2H, m), 3.92~3.99 (2H, m), 4.03~4.07 (2H, m), 5.00 (1H, t, J=4.4 Hz), 7.10 (1H, d, J=9.2 Hz), 7.16 (1H, q, J=2.8 Hz, 9.2 Hz), 7.35 (1H, d, J=2.8 Hz)

MS: (M+1$^+$)=391

Example 8

5-[2-(1-Benzyl-4-piperidyl)ethyl]-5H-6,7,8, 9tetrahydropyrid[3,2-b]azepin-6-one dihydrochloride

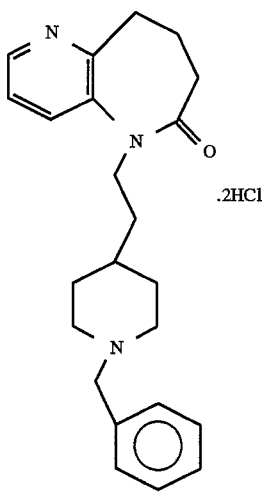

0.73 g of sodium hydride was washed with n-hexane and then suspended in 1 ml of N,N-dimethylformamide (DMF) and the suspension was stirred under cooling with ice. A solution of 0.989 g of 5H-6,7,8,9-tetrahydropyrid[3,2-b] azepin-6-one in 15 ml of DMF was added dropwise to the suspension. The mixture was stirred for 20 min at 60° C. The product was again cooled with ice and 2.51 g of 1-benzyl-4-(2-chloroethyl)piperidine hydrochloride was added thereto. The mixture was stirred for 2.5 h while keeping the outer temperature at 60° C. The solvent was distilled off and water was added to the residue. After extraction with methylene chloride followed by washing with a saturated aqueous sodium chloride solution and drying over magnesium sulfate, the solvent was distilled off. An oily product thus obtained was purified by silica gel column chromatography. The product was converted into its hydrochloride by an ordinary method to give 2.09 g of the intended compound in a colorless amorphous form.

Melting point: amorphous

Molecular formula: $C_{23}H_{29}N_3O \cdot 2HCl$

NMR (CDCl$_3$) δ: 1.21~2.04 (9H, m), 2.26 (4H, bs), 2.82 (4H, bd), 3.44 (2H, s), 3.81 (2H, bt), 7.08~7.45 (7H, m), 8.30 (1H, dd, J=1.3 Hz, 4.6 Hz)

MS: M$^+$=363 (DI-EI)

Example 9

3-[2-(1-Benzyl-4-piperidyl)ethyl]-2H-3,4-dihydro-6-methylpyrido[2,3-d]-m-oxazine-2-thione hydrochloride

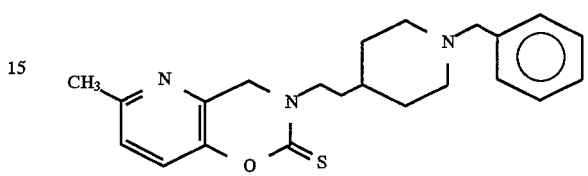

Excessive sodium borohydride was added to a Schiff base obtained by refluxing 0.50 g of 3-hydroxy-6-methyl-2-pyridinecarboxyaldehyde and 1.00 g of 1-benzyl-[4-(2-aminoethyl)]piperidine in methanol. The mixture was stirred at room temperature for 30 min and the reaction mixture was poured into a 0.2N aqueous sodium hydroxide solution. After extraction with ethyl acetate/diethyl ether followed by washing with a saturated sodium chloride solution, drying over anhydrous magnesium sulfate and distillation of the solvent under reduced pressure, the residue was dissolved in 30 ml of acetonitrile. 2.00 g of 1,1'-thiocarbonyldiimidazole was added to the solution and the reaction was conducted at 70° C. for 30 min. The liquid reaction mixture was poured into a 0.2N aqueous sodium hydroxide solution. After extraction with ethyl acetate/diethyl ether, followed by washing with a saturated sodium chloride solution and drying over anhydrous magnesium sulfate, the solvent was distilled off under reduced pressure. The residue was purified by silica gel column chromatography (methylene chloride:methanol=97:3). The resultant blue oily substance was converted into hydrochloride thereof and treated with Norit SX-3 to give 0.40 g of the intended compound in the form of light yellow crystals (yield: 26%).

Melting point: 138° to 139° C. (decomp.)

Molecular formula: $C_{22}H_{27}N_3OS \cdot HCl$

NMR (CDCl$_3$) δ: 1,16~2.10 (9H, m), 2.49 (3H, s), 2.64~2.97 (2H, m), 3.47 (2H, s), 3.96 (2H, t), 4.49 (2H, s), 6.95~7.40 (7H, m)

MS: (M+1$^+$)=382

Example 10

3-[2-{4 [(1-Benzyl)piperidyl]}ethyl]pyrazino[2, 3-d]-pyprimidine-2,4-dione fumarate

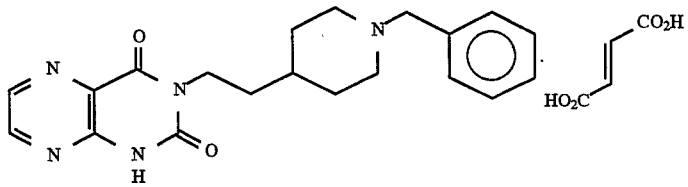

5 g of 3-aminopyrazine-2-carboxylic acid and 6.7 g of 1,1'-carbonyldiimidazole were suspended in 200 ml of acetonitrile and the suspension was heated under reflux for 6 h. An insoluble matter was removed by filtration and the residue was cooled to room temperature. Crystals thus formed were recovered by filtration to give 3.5 g of the acylimidazole derivative in the form of yellow needle-like crystals.

1.5 g of the acylimidazole derivative thus obtained and 1.4 g of 2-{4-[(1-benzyl)piperidyl]}-ethylamine were dissolved in 15 ml of tetrahydrofuran and the solution was stirred at room temperature overnight. Tetrahydrofuran was distilled off under reduced pressure and the residue was purified by silica gel column chromatography (methylene chloride:methanol=9:1) to give 1.9 g of the amide compound.

1.9 g of the amide compound and 2.2 g of 1,1'-carbonyldiimidazole were dissolved in 50 ml of acetonitrile and 50 ml of tetrahydrofuran and the solution was heated under reflux for 26 h. The solvent was distilled off under reduced pressure and water was added to the residue. After extraction with methylene chloride and drying over magnesium sulfate, the product was purified by silica gel column chromatography (methylene chloride:methanol=10:1) to recover 1.5 g of the amide compound and obtain 150 mg of the product. The product was converted into its fumarate by an ordinary method to give a powdery intended compound.

Melting point: 223° to 226° C. (decomp.)

Molecular formula: $C_{20}H_{23}N_5O_2 \cdot C_4H_4O_4$

NMR (CDCl$_3$) δ: 1.08~2.20 (9H, m), 2.76~3.08 (2H, m), 3.52 (2H, s), 3.80~4.24 (2H, m), 6.32 (1H, br s), 6.92~7.32 (5H, m), 8.52 (2H, s),

MS: (M+1$^+$)=366

Example 11

1-[2-{4-[(1-Benzyl)piperidyl]}ethyl]-7-hydroxy-7-methylpiperazino[2,3-c]pyrrolidin-2-one

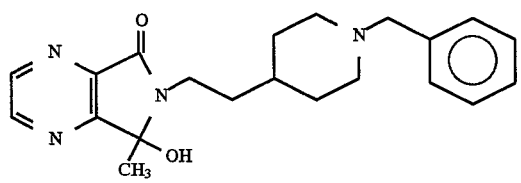

4.8 g of 2,3-pyrazinedicarboxylic anhydride and 7 g of 2-{4-[(1-benzyl)piperidyl]}ethylamine were heated under reflux in 70 ml of toluene for 2 h. The reaction mixture was cooled to room temperature and 10 g of N-[2-{4-{(1-benzyl)piperidyl]}ethyl]-2-pyrazincarboxamide-3-carboxylic acid thus formed was recovered by filtration.

1.76 g of the amido carboxylic acid compound thus obtained was heated at 70° C. in 25 ml of acetic anhydride for 30 min. The volatile substance was distilled off under reduced pressure and the residue was subjected to azeotropic distillation with toluene and then to the subsequent reaction without further purification.

The crude product thus obtained was dissolved in 20 ml of tetrahydrofuran and 2 ml of a 3M solution of methylmagnesium bromide in ether was added dropwise thereto at room temperature for 2 min. The mixture was stirred at room temperature for 30 min and an aqueous ammonium chloride solution was added thereto. After extraction with methylene chloride followed by drying over magnesium sulfate, the product was purified by silica gel column chromatography (methylene chloride:methanol=9:1) to give 0.15 g of the intended compound.

Melting point: amorphous

Molecular formula: $C_{21}H_{26}N_4O_2$

NMR(CDCl$_3$) δ: 1.00~2.24 (12H, m), 2.72~3.20 (2H, m), 3.40~3.72 (4H, m), 7.16~7.40 (5H, m), 8.52~8.68 (2H, dd)

MS: (M+1$^+$)=367

Example 12

1-[2-{4-[(1-Benzyl)piperidyl]}ethyl]-7-methylenepiperazino[2,3-c]pyrrolidin-2-one fumarate

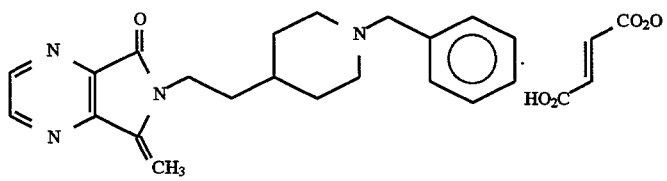

0.1 g of 1-[2-{4-[(1-benzyl)piperidyl]}ethyl]-7-hydroxy-7-methylpiperazino[2,3-c]pyrrolidin-2-one was dissolved in 3 ml of acetic anhydride and the solution was heated under reflux for 3.5 h. The volatile matter was distilled off under reduced pressure and the residue was purified by silica gel column chromatography (methylene chloride:methanol= 9:1) to give 0.06 g of the product. It was converted into fumarate thereof by an ordinary method to give the intended compound.

Melting point: amorphous

Molecular formula: $C_{21}H_{24}N_4O \cdot C_4H_4O_4$

NMR (CDCl$_3$) δ: 1.04~2.20 (9H, m), 2.68~3.04 (2H, m), 3.48 (2H, s), 3.76~4.04 (2H, t), 5.04~5.12 (1H, d), 5.72~5.80 (1H, d), 7.12~7.40 (5H, m), 8.64~8.80 (2H, dd)

MS: (M+1$^+$)=349

Example 13

1-[2-{4-[(1-Benzyl)piperidyl]}ethyl]-4-benzoylpyrrolidin-2-one hydrochloride

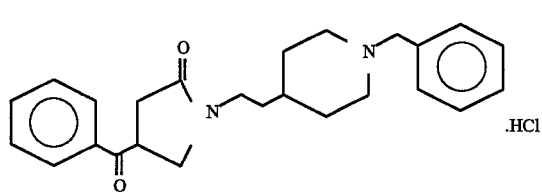

(1) Synthesis of 1-[2-{4-[(1-benzyl)piperidyl]}-ethyl] pyrrolidin-1-one-4-carboxylic acid

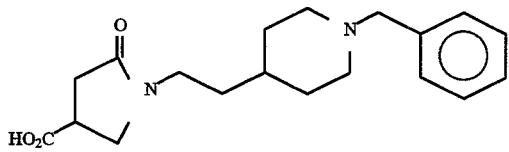

12 g of itaconic acid and 20 g of 4-(2-aminoethyl)-1-benzylpiperidine were melted at 150° to 160° C. for 2 h 15 min. The reaction mixture was extracted with water and the aqueous layer was washed with methylene chloride. Water was distilled off under reduced pressure and the residue was subjected to azeotropic distillation with toluene to give 27 g of the crude carboxylic acid.

(2) Synthesis of 1-[2-{4-{(1-benzyl)piperidyl]}-ethyl]-4-benzoylpyrrolidin-2-one hydrochloride

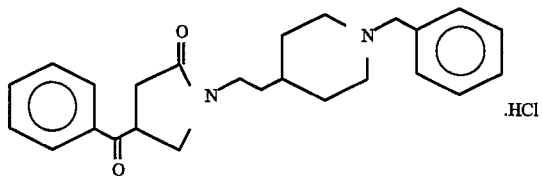

4.3 g of the crude carboxylic acid obtained in the above process (1) was dissolved in 80 ml of methylene chloride and 5 ml of thionyl chloride was added dropwise to the solution at room temperature for 5 min. The mixture was stirred for additional 10 min at room temperature and the volatile substance was distilled off under reduced pressure.

The residue was dissolved in 70 ml of methylene chloride and 12 ml of benzene was added to the solution and cooled with ice. 5.5 g of aluminum chloride was added thereto for 5 min. After stirring at room temperature overnight, the reaction mixture was poured into ice, made basic with sodium hydroxide, extracted with methylene chloride and dried over magnesium sulfate. Methylene chloride was distilled off under reduced pressure and 6 g of the crude product was purified by silica gel column chromatography (methylene;chloridemethanol=9:1) to give 1 g of the free base. It was converted into hydrochloride thereof by an ordinary method to give the intended compound in the form of a hygroscopic amorphous substance.

Melting point: amorphous

Molecular formula: $C_{25}H_{30}N_2O_3 \cdot HCl$

NMR (CDCl$_3$) δ: 1.00~4.28 (20H, m), 7.04~6.68 (5H, m), 7.72~b 8.00 (2H, m)

MS: (M+1$^+$)=391

Example 14

1-[2-{(4-[(1-Benzyl)piperidyl]}ethyl]-4-benzylpyrrolidin-2-one hydrochloride

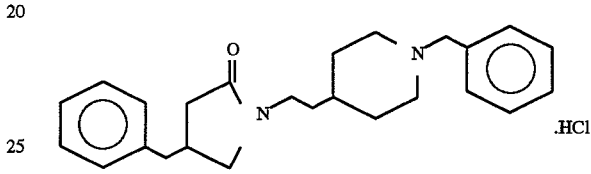

0.58 g of 1-[2{4-[(1-benzyl)piperidyl]}ethyl]-4-benzoylpyrrolidin-2-one was dissolved in 10 ml of methanol and 60 mg of sodium borohydride was added to the solution at room temperature. The mixture was stirred for 10 min. Methanol was distilled off under reduced pressure and water was added to the residue. After extraction with methylene chloride followed by drying over magnesium sulfate, methylene chloride was distilled off under reduced pressure. The product was purified by silica gel column chromatography (methylene chloride:methanol=9:1) t6 give 0.41 g of the alcohol compound in the form of a colorless, viscous, oily mixture of two isomers, which was subjected to the subsequent reaction without separation.

0.41 g of the alcohol compound produced above was dissolved in 5 ml of pyridine and 0.22 ml of p-toluyl chlorothionoformate was added to the solution at room temperature. The mixture was stirred for 3 h and water was added thereto. After extraction with ethyl acetate followed by drying over magnesium sulfate, ethyl acetate was distilled off under reduced pressure. The product was purified by silica gel column chromatography (methylene chloride methanol=95:5) to give 0.4 g of the thiocarbonate compound in the form of a brown oil.

0.39 g of the thiocarbonate compound produced above was dissolved in 9 ml of toluene and 0.5 ml of tributyltin hydride and a catalytic amount of 2,2'-azobis (isobutyronitrile) were added thereto. The mixture was heated at 70° to 80° C. for 8 h. Toluene was distilled off under reduced pressure and the residue was purified by silica gel column chromatography (methylene chloride:methanol= 9:1) to give 0.12 g of the free base. It was converted into hydrochloride thereof by an ordinary method to give the intended amorpous compound.

Melting point: amorphous

Molecular formula: $C_{25}H_{32}N_2O \cdot HCl$

NMR (CDCl$_3$) δ: 1,16~3.48 (20H, m), 3.52 (2H, s), 7.00~7.40 (10H, m)

MS: M$^+$=376 (FD)

Example 15

3-{2-[1-(1, 3-Dioxolan-2-ylmethyl)-4-piperidine]ethyl}-5-methoxy-1,2,3,4-tetrahydroquinazoline-2,4-dione hydrochloride

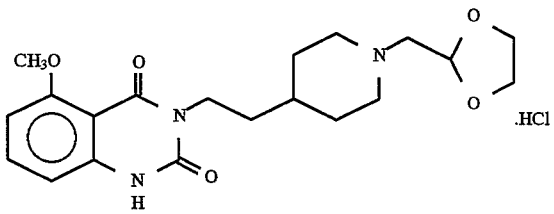

1.8 g of 1-(2-amino-6-methoxybenzenecarbonyl)imidazole and 2.14 g of 1-(1,3-dioxolan-2-ylmethyl)-4-(2-aminoethyl)piperidine were dissolved in 150 ml of tetrahydrofuran and stirred at room temperature for 2 h. Then the solvent was distilled off and the residue was dissolved in 100 ml of tetrahydrofuran. 3.7 g of N,N'-carbonyldiimidazole was added to the solution and refluxed overnight. The solvent was distilled off and methylene chloride was added to the residue. It was washed with water and the solvent was dried over anhydrous magnesium sulfate. After filtration followed by distillation of the solvent, the resulting oil was purified by silica gel column chromatography to give a product in the form of white crystals, which was converted into hydrochloride thereof by an ordinary method to give 1.6 g of the intended compound in amorphous form.

Melting point: amorphous

Molecular formula: $C_{20}H_{27}N_3O_5 \cdot HCl$

NMR (CDCl$_3$) δ: 1.20~2.20 (9H, m), 2.60 (2H, d), 2.98 (2H, d), 3.69~4.20 (6H, m), 3.97 (3H, s), 5.03 (1H, m), 6.56~6.74 (2H, m), 7.50 (1H, dd)

MS: (M+1$^+$)=390

Example 16

3-{2-[1-(1,3-Dioxolan-2-ylmethyl)-4-piperidyl]ethyl}-1,2,3,4-tetrahydroquinazolin-2-one hydrochloride

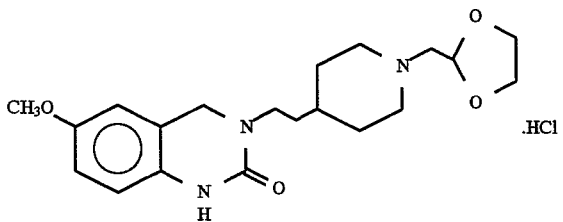

15 ml of methanol was added to 1.0.4 g of 1-(1,3-dioxolan-2-ylmethyl)-4-(2-aminoethyl)piperidine to give a solution and a solution of 1.47 g of 2-amino-5-methoxybenzaldehyde in 30 ml of methanol was added to the solution. The mixture was stirred at room temperature for 0 min and cooled with ice. Sodium borohydride was added in portions to the reaction mixture to conduct reduction. The solvent was distilled off and water was added to the residue. After extraction with ethyl acetate followed by drying over magnesium sulfate, the solvent was distilled off and the resultant oily substance was dissolved in 30 ml of tetrahydrofuran. 2.42 g of N,N'-carbonyldiimidazole was added to the solution and heated under reflux for 2.5 h. The solvent was distilled off and the resulting oily substance was purified by silica gel column chromatography. The product was converted into hydrochloride thereof by an ordinary method to give 0.19 g of the intended compound in the form of a light yellow amorphous substance.

Melting point: amorphous

Molecular formula: $C_{20}H_{29}N_3O_5 \cdot HCl$

NMR(CDCl$_3$) δ: 1.20~1.38 (3H, m), 1.52~1.54 (2H, bq), 1.71 (2H, bd), 2.04 (2H, t, J=9.2 Hz), 2.54 (2H, d, J=4.6 Hz), 2.97 (2H, bd), 3.44 (2H, t, J=7.4 Hz), 3.66 (3H, s), 3.80~3.84 (2H, m), 3.92~3.95 (2H, m), 4.99 (1H, t, J=4.6 Hz), 6.57 (1H, d, J=3.2 Hz), 6.62 (1H, d, J=8.4 Hz), 6.70 (1H, q, J=3.2 Hz, 8.4 Hz)

MS: (M+1$^+$)=376

Example 17

3-{2-[1-(1,3-Dioxolan-2-ylmethyl)-4-piperidyl]ethyl-6-methoxy-1,2 3,4-tetrahydroquinazoline-2,4-dione

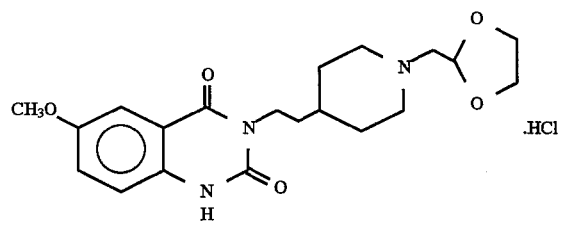

10 ml of tetrahydrofuran was added to 0.83 g of 1-(1,3-dioxolan-2-ylmethyl)-4-(2-aminoethyl)piperidine to give a solution and 0.93 g of 1-(2-amino-5-methoxybenzenecarbonyl)imidazole was added to the solution. The mixture was stirred. 1.26 g of N,N'-carbonyldiimidazole was added to the solution and the mixture was heated under reflux for 19 h. The solvent was distilled off and the resulting oily substance was purified by silica gel column chromatography. The product was converted into hydrochloride thereof by an ordinary method to give 0.30 g of the intended compound in the form of a light yellow amorphous substance.

Melting point: amorphous

Molecular formula: $C_{20}H_{27}N_3O_5 \cdot HCl$

NMR (CDCl$_3$) δ: 1.36 (3H, bs), 1.59~1.64 (2H, m), 1.76 (2H, bd), 2.05 (2H, bt), 2.53 (2H, d, J=4.6 Hz), 2.98 (2H, bd), 3.80~3.83 (2H, m), 3.83 (3H, s), 3.91~3.93 (2H, m), 4.08 (2H, bt), 4.98 (1H, t, J=4.6 Hz), 7.04 (1H, d, J=8.8 Hz), 7.18 (1H, q, J=2.8 Hz, 8.8 Hz), 7.49 (1H, d, J=2.8 Hz), 11.05 (1H, bs)

MS: (M+H$^-$)=390

Examples 18 to 75

The following compounds were produced in the same manner as that of Examples 1 to 17. The Arabic numerals refer to Example Numbers.

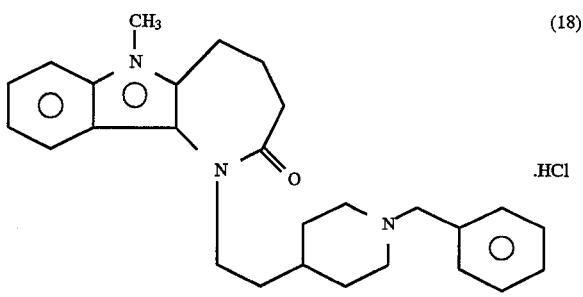

(18)

Melting point: amorphous

Molecular formula: $C_{27}H_{33}N_3O \cdot HCl$

NMR (CDCl$_3$) δ: 1.2~2.1 (9H, m), 2.31 (4H, bs), 2.78 (4H, bd) 3.41 (2H, s), 3.67 (3H, s), 3.90 (2H, bt), 7.02~7.46 (9H, m)

MS: M$^+$=415 (FD)

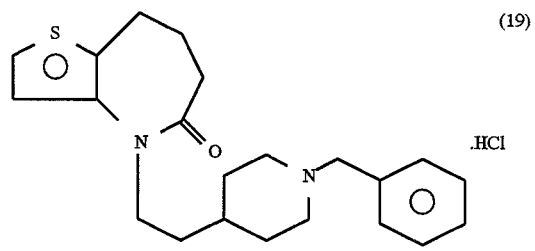

(19)

Melting point: amorphous

Molecular formula: $C_{22}H_{28}N_2OS \cdot HCl$

NMR (CDCl$_3$) δ: 1.18~2.01 (9H, m), 2.26~2.30 (4H, m), 2.68~2.88 (4H, m), 3.41 (2H, s), 3.67 (2H, bt), 6.79 (1H, d, J=5.7 Hz), 7.00 (1H, d, J=5.7 Hz), 7.18 (5H, s)

MS: M$^+$=368 (FD)

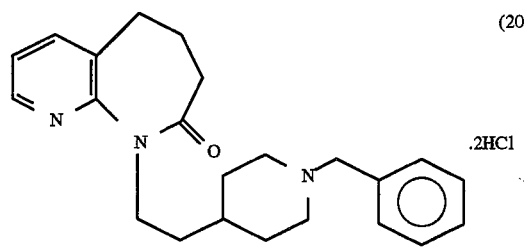

(20)

Melting point: amorphous

Molecular formula: $C_{23}H_{29}N_3 \cdot 2HCl$

NMR (CDCl$_3$) δ: 1.20~1.86 (9H, m), 2.24~2.29 (4H, m), 2.59~2.81 (4H, m), 3.43 (2H, s), 4.05 (2H, bt), 7.01 (1H, dd, J=4.9 Hz, 7.5 Hz), 7.20 (5H, s), 7.46 (1H, dd, J=1.8 Hz, 7.5 Hz), 8.29 (1H, dd, J=1.8 Hz, 4.9 Hz)

MS: (M+1$^+$)=364 (FAB)

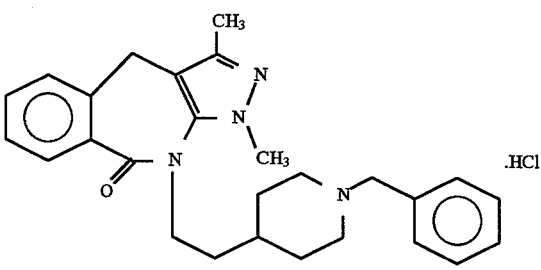

(21)

Melting point: amorphous

Molecular formula: $C_{27}H_{32}N_4O \cdot HCl$

NMR (CDCl$_3$) δ: 1.24~2.04 (11H, m), 2.18 (3H, s), 2.83 (2H, bd), 3.37~3.48 (4H, m), 3.64 (3H, s), 6.96~7.36 (8H, m), 7.62 (1H, dd, J=2.8 Hz, 5.5 Hz)

MS: (M+1$^+$)=429 (FAB)

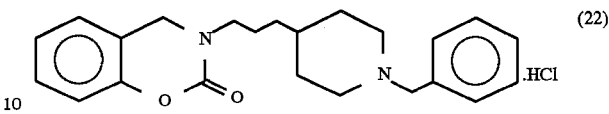

(22)

Melting point: 217.6°~218.8° C.

Molecular formula: $C_{23}H_{28}N_2O_2 \cdot HCl$

NMR (CDCl$_3$) δ: 1.16~2.04 (11H, m), 2.83 (2H, bd), 2.40 (2H, t, J=7.2 Hz), 2.43 (2H, s), 4.39 (2H, s), 6.88~7.35 (9H, m)

MS: M$^+$=364 (DI-EI)

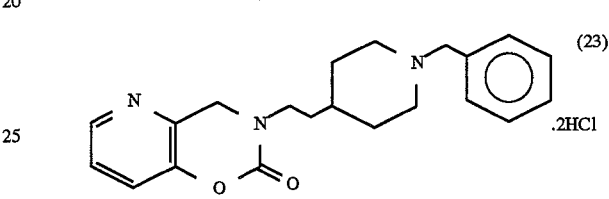

(23)

Melting point: amorphous

Molecular formula: $C_{21}H_{25}N_2O_3 \cdot 2HCl$

NMR (CDCl$_3$) δ: 1.28~2.04 (9H, m), 2.85 (2H, bd), 2.45 (2H, s), 2.50 (2H, t, J=7.3 Hz), 4.49 (2H, s), 7.02~7.32 (7H, m), 8.24 (1H, dd, J=2.1 Hz, 4.1 Hz)

MS: (M+1$^+$)=352 (FAB)

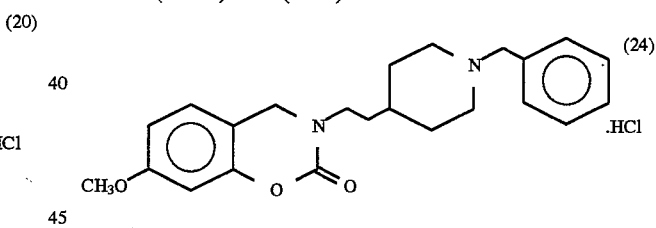

(24)

Melting point: 209.5°~210.7° C.

Molecular formula: $C_{23}H_{28}N_2O_3 \cdot HCl$

NMR (CDCl$_3$) δ: 1.22~2.12 (9H, m), 2.89 (2H, bd), 3.48 (2H, t, J=7.3 Hz), 3.51 (2H, s), 3.76 (3H, s), 4.35(2H, s), 6.59(1H, dd, J=2.8 Hz, 13.1 Hz), 6.94 (1H, d, J=13.1 Hz.), 7.18~7.38 (6H, m)

MS: (M+1$^+$)=381 (FAB)

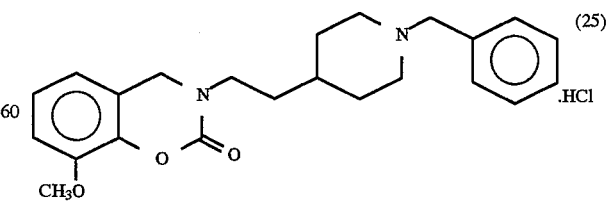

(25)

Melting point: amorphous

Molecular formula: $C_{23}H_{28}N_2O_3 \cdot HCl$

NMR (CDCl₃) δ: 1.16~2.12 (9H, m), 2.85 (2h, bd), 3.38~3.55 (4H, m), 3.83 (3H, s), 4.37 (2H, s), 6.54~7.00 (3H, m), 7.24 (5H, s)

MS: (M+1⁺)=381 (FAB)

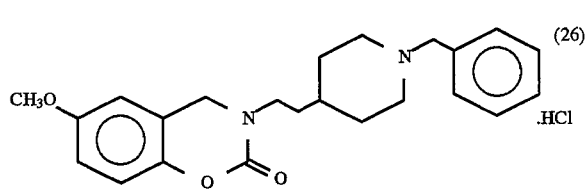

Melting point: 209.8°~210.9° C. (decomp.)

Molecular formula: $C_{23}H_{28}N_2O_3 \cdot HCl$

NMR (CDCl₃) δ: 1,19~2.11 (9H, m), 2.87 (2H, bd), 3.43 (2H, t, J=7.5 Hz), 3.48 (2H, s), 3.94 (3H, s), 4.35 (2H, s), 6.60 (1H, dd, J=2.6 Hz, 9.8 Hz), 6.78 (1H, d, J=2.6 Hz), 6.91 (1H, d, J=9.8 Hz), 7.24 (5H, s)

MS: (M+1⁺)=381 (FAB)

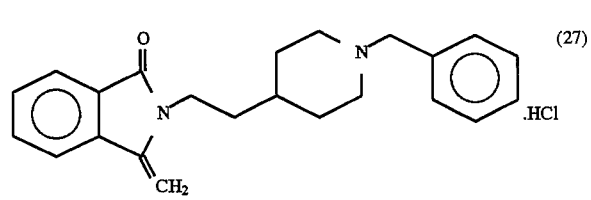

Melting point: amorphous

Molecular formula: $C_{23}H_{26}N_2O \cdot HCl$

NMR (CDCl₃) δ: 1.18~2.11 (9H, m), 2.85 (2H, bd), 3.47 (2H, s), 3.76 (2H, t, J=7.3 Hz), 4.78 (1H, d, J=2.3 Hz) 5.14 (1H, d, J=2.3 Hz), 7.24 (5H, s), 7.38~7.81 (4H, m)

MS: (M+1⁺)=347 (FAB)

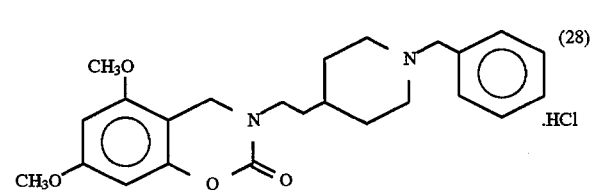

Melting point: amorphous

Molecular formula: $C_{24}H_{30}N_2O_4 \cdot HCl$

NMR (CDCl₃) δ: 1.24~2.12 (9H, m), 2.88 (2H, bd), 3.38~356 (4H, m), 3.75 (3H, s), 3.78 (3H, s), 4.24 (2H, s), 6.15 (1H, bs), 720~7.30 (6H, bs)

MS: (M+1⁺)=411 (FAB)

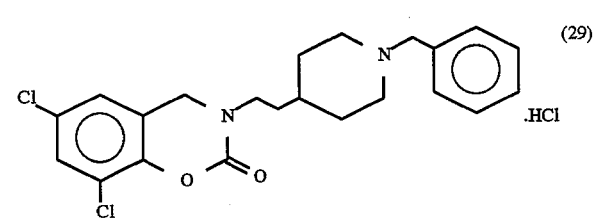

Melting point: 220.5°~221.8° C. (decomp.)

Molecular formula: $C_{22}H_{24}Cl_2N_2O_2 \cdot HCl$

NMR (CDCl₃) δ: 1.24~2.20 (9H, m), 2.95 (2H, bd), 3.36~3.56 (4H, m), 4.38 (2H, s), 6.96 (1H, bs), 7.29 (6H, bs)

MS: (M+1⁺)=419 (FAB)

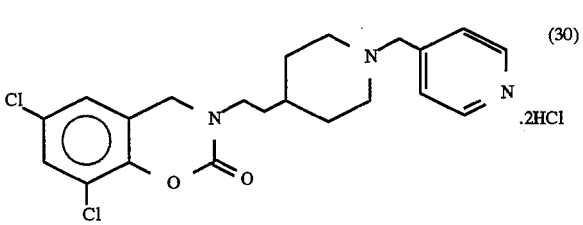

Melting point: amorphous

Molecular formula: $C_{21}H_{23}Cl_2N_3O_2 \cdot 2HCl$

NMR (CDCl₃) δ: 1.20~1.12 (9H, m), 2.78 (2H, bd), 3.36~3.53 (4H, m), 4.36 (2H, s), 6.92 (1H, d, J=2.3 Hz), 7.08~7.28 (3H, m), 8.41 (2H, d, J=8.5 Hz)

MS: (M+1⁺)=420 (FAB)

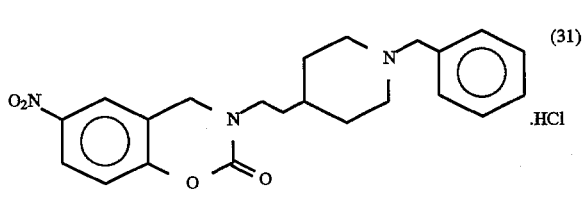

Melting point: 231.1°~232.3° C. (decomp.)

Molecular formula: $C_{22}H_{25}N_3O_4 \cdot HCl$

NMR (CDCl₃) δ: 1.16~2.09 (9H, m), 2.84 (2H, bd), 2.40~2.56 (4H, m), 4.47 (2H, s), 7.06 (1H, d, J=9.3 Hz), 7.23 (5H, s), 7.97 (1H, d, J=2.6 Hz), 8.08 (1H, dd, J=2.6 Hz, 9.3 Hz)

MS: (M+1⁺)=396 (FAB)

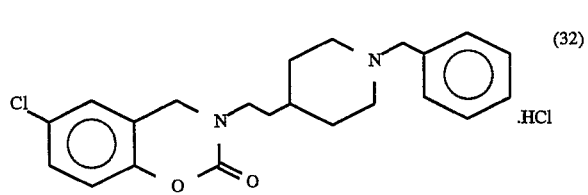

Melting point: 22.53°~227.1° C. (decomp.)

Molecular formula: $C_{22}H_{25}ClN_2O_2 \cdot HCl$

NMR (CDCl₃) δ: 1.20~2.08 (9H, m), 2.83 (2H, bd), 3.35~3.52 (4H, m), 4.33 (2H, s), 6.85 (1H, d, J=9.0 Hz), 7.04 (1H, dd, J=2.8 Hz, 9.0 Hz), 7.22 (6H, bs)

MS: (M+1⁺)=385 (FAB)

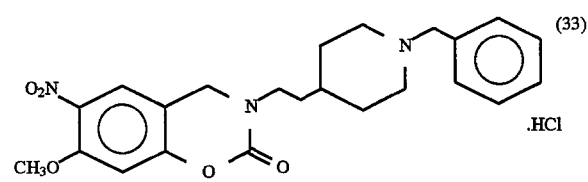

Melting point: amorphous

Molecular formula: $C_{24}H_{30}N_2O_4 \cdot HCl$

NMR (CDCl₃) δ: 1.16~2.12 (9H, m), 2.84 (2H, bs), 3.36~3.52 (4H, m), 3.81 (6H, s), 4.31 (2H, s), 6.47 (1H, d, J=1.8 Hz), 7.22 (6H, bs)

MS: (M+1⁺)=411 (FAB)

(34)

Melting point: 189.1°~189.8° C.

Molecular formula: C₂₁H₂₄N₄O₄·2HCl

NMR (CDCl₃) δ: 1.21~2.15(9H, m), 2.82 (2H, bd), 3.42~3.62 (4H, m), 4.56 (2H, s), 7.06 (1H, d, J=8.2 Hz), 7.24 (2H, d, J=6.2 Hz), 8.03~8.15 (2H, m), 8.44 (2H, d, J=6.2 Hz)

MS: (M+1⁺)=397 (FAB)

(35)

Melting point: amorphous

Molecular formula: C₂₂H₂₇N₃O₂·2HCl

NMR (CDCl₃) δ: 1.16~2.07 (9H, m), 2.82 (2H, bd), 3.32~3.48 (4H, m), 3.92 (2H, bs), 4.24 (2H, s), 6.30 (1H, d, J=2.3 Hz), 6.46 (1H, q, J=2.3 Hz, 8.7 Hz), 6.72 (1H, d, J=8.7 Hz), 7.22 (5H, bs)

MS: (M+1⁺)=366 (FAB)

(36)

Melting point: amorphous

Molecular formula: C₂₄H₂₉N₃O₃·HCl

NMR(CDCl₃) δ: 1.16~2.12 (9H, m), 2.14 (3H, s), 2.84 (2H, bd), 3.45 (4H, bs), 4.33 (2H, s), 6.78 (1H, d, J=9.5 Hz), 7.14~7.28 (6H, m), 7.63 (1H, bs), 9.00 (1H, s)

MS: (M+1⁺)=408 (FAB)

(37)

Melting point: amorphous

Molecular formula: C₂₃H₂₆N₂O₃·HCl

NMR (CDCl₃) δ: 1,24~2.12 (9H, m), 2.40 (3H, s), 2.86 (2H, bd), 3.47 (2H, s), 4.00 (2H, bt), 7.00~7.44 (7H, m), 7.76 (1H, bs)

MS: (M+1⁺)=379 (FAB)

(38)

Melting point: 195.1°~195.8° C.

Molecular formula: C₂₃H₂₆N₂O₄·HCl

NMR (CDCl₃) δ: 1.34 (3H, bs), 1.65 (2H, bs), 1.74 (2H, bs), 1.95 (2H, bt), 2.87 (2H, bd), 3.48 (2H, s), 3.86 (3H, s), 4.05 (2H, dt, J=2.0 Hz, 7.2 Hz), 7.19 (1H, d, J=9.4 Hz), 7.24 (1H, q, J=3.0 Hz, 9.4 Hz), 7.31 (5H, bs) 7.45 (1H, d, J=3.0 Hz)

MS: (M+1⁺)=395 (FAB)

(39)

Melting point: 199.5°~200.4° C.

Molecular formula: C₂₂H₂₃FN₂O₃·HCl

NMR (CDCl₃) δ: 1.34 (3H, bs), 1.63~1.66 (2H, m), 1.73~1.77 (2H, m), 1.95 (2H, bt), 2.86 (2H, bd), 3.48 (2H, s), 4.04 (2H, dt, J=4.0 Hz, 5.2 Hz), 7.23~7.28 (6H, m), 7.37~7.42 (1H, m), 7.71~7.73 (1H, m)

MS: (M+1⁺)=383 (FAB)

(40)

Melting point: 209.4°~210.6° C. (decomp.)

Molecular formula: C₁₉H₂₃FN₂O₅·HCl

NMR (CDCl₃) δ: 1.34~1.41 (3H, m), 1.60~1.66 (2H, bq), 1.73~1.76 (2H, bd), 2.06 (2H, t, J=11.2 Hz), 2.55 (2H, d, J=4.4 Hz), 2.98 (2H, bd), 3.83~3.86 (2H, m), 3.94~3.98 (2H, m), 4.02~4.06 (2H, m), 4.99 (1H, t, J=4.4 Hz), 7.25~7.28 (1H, m), 7.37~7.42 (1H, m), 7.72 (1H, q, J=2.6 Hz, 7.2 Hz)

MS: (M+1⁺)=379 (FAB)

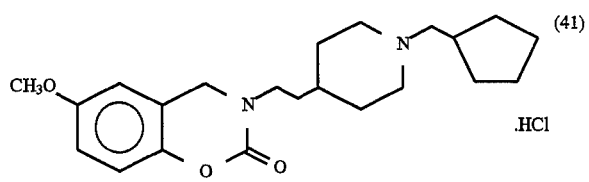

Melting point: 210.5°~211.4° C. (decomp.)

Molecular formula: $C_{22}H_{32}N_2O_3 \cdot HCl$

NMR (CDCl$_3$) δ: 1.15~1.20 (2H, m), 1.25~1.38 (3H, m), 1.51~1.60 (6H, m), 1.72~1.78 (4H, m), 1.93 (2H, t, J=9.6 Hz), 2.06 (1H, m), 2.25 (2H, dd, J=2.0 Hz, 7.2 Hz), 2.91 (2H, bd), 3.45~3.49 (2H, m), 3.75 (3H, s), 4.38 (2H, s), 6.58 (1H, s), 6.76 (1H, d, J=10.0 Hz), 6.91 (1H, d, J=10.0 Hz)

MS: (M+1⁺)=373 (FAB)

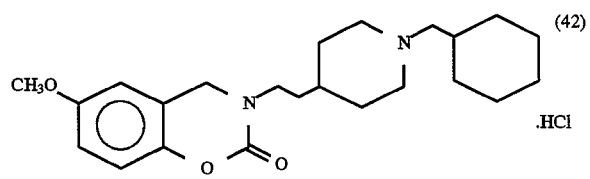

Melting point: 206.5°~207.8° C.

Molecular formula: $C_{23}H_{34}N_2O_3 \cdot HCl$

NMR (CDCl$_3$) δ: 0.81~0.89 (2H, m), 1.09~1.23 (3H, m), 1.23~1.35 (2H, m), 1.46 (1H, m), 1.54~1.76 (10H, m), 1.84 (2H, bt), 2.08 (2H, d, J=7.2 Hz), 2.84 (2H, bd), 3.49 (2H, m), 3.76 (3H, s), 4.41 (2H, s), 6.60 (1H, d, J=2.8 Hz), 6.78 (1H, dd, J=2.8 Hz, 8.8 Hz), 6.92 (1H, d, J=8.8 Hz)

MS: (M+1⁺)=387 (FAB)

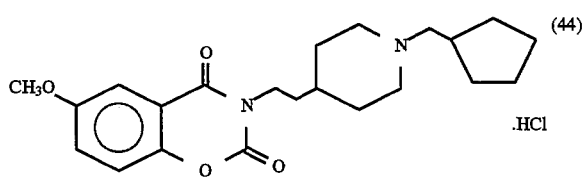

Melting point: 205.9°~207.2° C. (decomp.)

Molecular formula: $C_{23}H_{32}N_2O_4 \cdot HCl$

NMR (CDCl$_3$) δ: 0.84~0.92 (2H, m), 1.15~1.25 (3H, m), 1.36~1.42 (2H, m), 1.51 (1H, m), 1.63~1.78 (10H, m), 1.93 (2H, t, J=10.6 Hz), 2.15 (2H, d, J=7.2 Hz), 2.91 (2H, bd), 3.87 (3H, s), 4.06 (2H, m), 7.19 (1H, d, J=8.8 Hz), 7.25 (1H, dd, J=2.8 Hz, 8.8 Hz), 7.45 (1H, d, J=2.8 Hz)

MS: (M+1⁺)=401 (FAB)

Melting point: 119.5°~120.8° C.

Molecular formula: $C_{21}H_{26}N_2O_4 \cdot C_4H_4O_4$

NMR (CDCl$_3$) δ: 1.28~1.33 (3H, m), 1.58~1.62 (2H, m), 1.63~1.75 (2H, m), 1.93 (2H, bt), 2.90 (2H, bd), 3.37 (2H, s), 3.50 (2H, m), 3.78 (3H, s), 4.41 (2H, s), 6.38 (1H, dd, J=0.8 Hz, 1.6 Hz), 6.60 (1H, d, J=2.8 Hz), 6.79 (1H, dd, J=2.8 Hz, 8.8 Hz), 6.95 (1H, d, J=8.8 Hz), 7.32 (1H, dd, J=0.8 Hz, 1.6 Hz), 7.37(1H, t, J=1.6 Hz)

MS: (M+1⁺)=371 (FAB)

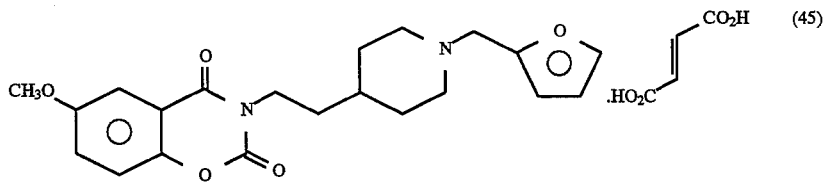

Melting point: 155.3°~156.0° C.

Molecular formula: $C_{21}H_{24}N_2O_5 \cdot C_4H_4O_4$

NMR (CDCl$_3$) δ: 1.30~1.43 (3H, m), 1.62~1.68 (2H, m), 1.76~1.80 (2H, m), 1.99 (2H, bt), 2.89 (2H, bd), 3.52 (2H, s), 3.87 (3H, s), 4.04 (2H, m), 6.18 (1H, d, J=3.2 Hz), 6.31 (1H, dd, J=3.2 Hz, 6.4 Hz), 7.19 (1H, d, J=8.8 Hz), 7.20~7.28 (2H, m), 7.36~7.37 (1H, m), 7.45 (1H, d, J=3.2 Hz)

MS: (M+1⁺)=385 (FAB)

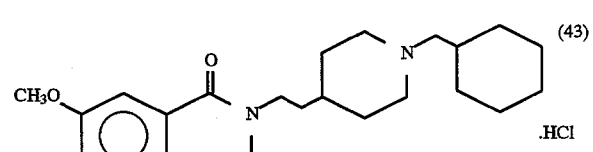

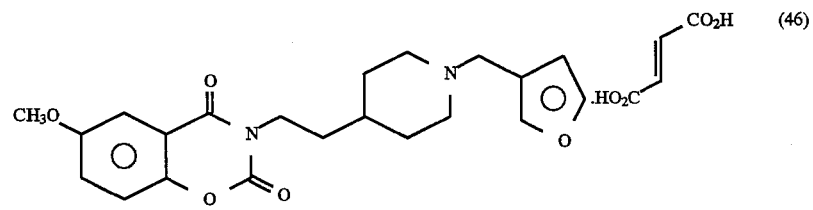

Melting point: 162.9°~163.6° C.

Molecular formula: $C_{21}H_{24}N_2O_5 \cdot C_4H_4O_4$

NMR (CDCl$_3$) δ: 1.30~1.38 (3H, m), 1.62~1.66 (2H, m), 1.77~1.79 (2H, m), 1.94 (2H, bt), 1.90 (2H, bd), 3.37 (2H, s), 3.87 (3H, s), 4.05 (2H, m), 6.38 (1H, bs), 7.19 (1H, d, J=9.2 Hz), 7.24 (1H, dd, J=2.8 Hz, 9.2 Hz), 7.32(1H, bs), 7.37 (1H, bs), 7.44 (1H, d, J=2.8 Hz)

MS: (M+1$^+$)=385 (FAB)

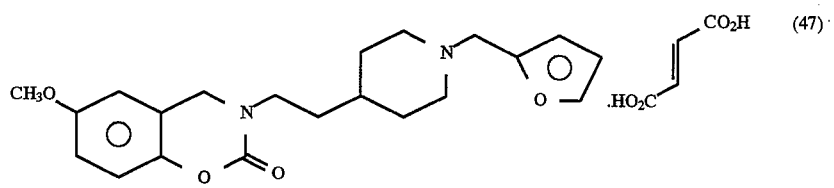

(47)

Melting point: 113.3°~113.8° C.

Molecular formula: $C_{21}H_{26}N_2O_4 \cdot C_4H_4O_4$

NMR (CDCl$_3$) δ: 1.31~1.38 (3H, m), 1.56~1.62 (2H, m), 1.73 (2H, bd), 1.97 (2H, t, J=11.0 Hz), 2.88 (2H, bd), 3.48 (2H, m), 3.51 (2H, s), 3.77 (3H, s), 4.40 (2H, s), 6.18 (1H, d, J=3.2 Hz), 6.30 (1H, dd, J=2.0 Hz, 3.2 Hz), 6.59 (1H, d, J=2.8 Hz), 6.79 (1H, dd, J=2.8 Hz, 8.8 Hz), 6.93 (1H, d, J=8.8 Hz), 7.36 (1H, d, J=2.0 Hz)

MS: (M+1$^+$)=371 (FAB)

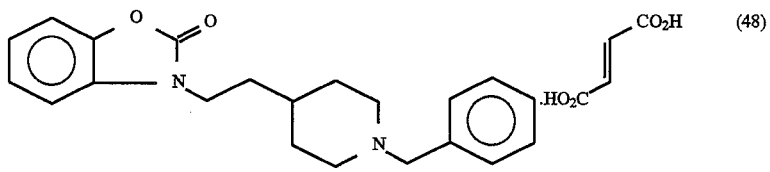

(48)

Melting point: 176.2°~176.8° C.

Molecular formula: $C_{21}H_{24}N_2O_2 \cdot C_4H_4O_4$

NMR (CDCl$_3$) δ: 1.31~1.36 (3H, m), 1.69~1.76 (4H, m), 1.95 (2H, bt), 2.88 (2H, bd), 3.49 (2H, s), 3.85 (2H, t, J=7.4 Hz), 6.95 (1H, d, J=7.6 Hz), 7.10~7.31 (8H, m)

MS: (M+1$^+$)=337 (FAB)

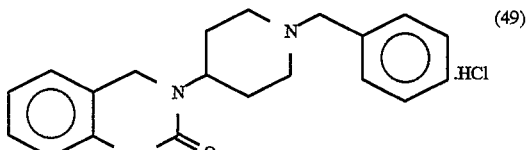

(49)

Melting point: 217.9°~219.2° C. (decomp.)

Molecular formula: $C_{20}H_{22}N_2O_2 \cdot HCl$

NMR (CDCl$_3$) δ: 1.72~1.78 (2H, m), 1.84~1.94 (2H, m), 2.11~2.16 (2h, m), 2.99 (2H, bd), 3.52 (2H, s), 4.33 (1H, m), 4.39 (2H, s), 7.03 (1H, d, J=8.0 Hz), 7.10~7.11 (2H, m), 7.24~7.33 (6H, m)

MS: (M+1$^+$)=323 (FAB)

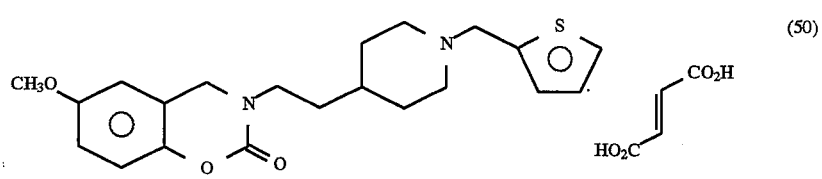

(50)

Melting point: 178.5°~179.1° C.

Molecular formula: $C_{21}H_{26}N_2O_2S \cdot C_4H_4O_4$

NMR (CDCl$_3$) δ: 1.28~1.38 (3H, m), 1.57~1.61 (2H, m), 1.71~1.73 (2H, m), 1.98 (2H, bt), 2.91 (2H, bd), 3.48 (2H, m), 3.70 (2H, s), 3.76 (3H, s), 4.39 (2H, s), 6.59 (1H, d, J=1.2 Hz), 6.78 (1H, dd, J=1.2 Hz, 8.8 Hz), 6.88~6.94 (3H, m), 7.20 (1H, d, J=4.8 Hz)

MS: M$^+$=386 (DI-EI)

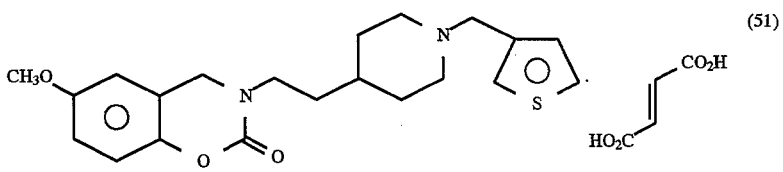

(51)

Melting point: 188.3°~189.2° C.

Molecular formula: $C_{21}H_{26}N_2O_3S \cdot C_4H_4O_4$

NMR (CDCl$_3$) δ: 1.24~1.36 (3H, m), 1.61~1.63 (2H, m), 1.72~1.74 (2H, m), 1.92 (2H, bt), 2.89 (2H, bd), 3.48~3.53 (2H, m), 3.53 (2H, s), 3.78 (3H, s), 4.41 (2H, s), 6.60 (1H, d, J=2.8 Hz), 6.79 (1H, dd, J=2.8 Hz, 8.8 Hz), 6.96 (1H, d, J=8.8 Hz), 7.05 (1H, dd, J=0.8 Hz, 5.0 Hz), 7.11 (1H, bs), 7.25~7.27 (1H, bs)

MS: M$^+$=386 (DI-EI)

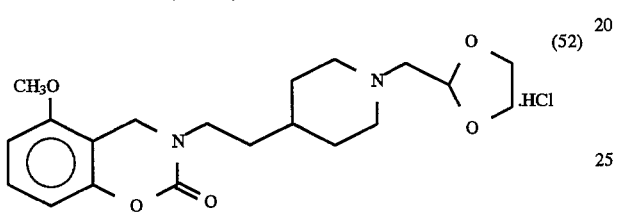

(52)

Melting point: amorphous

Molecular formula: $C_{20}H_{28}N_2O_5 \cdot HCl$

NMR (CDCl$_3$) δ: 1.26~1.43 (3H, m), 1.59~1.67 (2H, m), 1.74 (2H, bd), 2.08 (2H, t), 2.56 (2H, d), 3.00 (2H, d), 3.52 (2H, t), 3.83~3.90 (2H, m), 3.86 (3H, s), 3.92~4.00 (2H, m), 4.37 (2H, s), 5.00 (1H, dd), 6.63 (2H, dd), 7.21 (1H, t)

MS: (M+1$^+$)=377 (FAB)

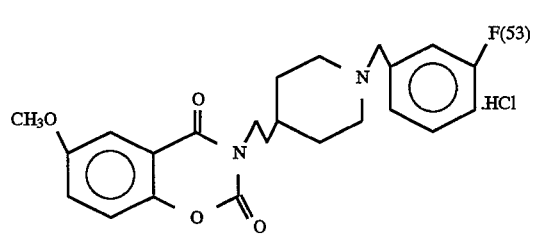

(53)

Melting point: 194°~195° C.

Molecular formula: $C_{23}H_{25}N_2O_4F \cdot HCl$

NMR (CDCl$_3$) δ: 1.30~1.41 (3H, m), 1.62~1.70 (2H, m), 1.76 (2H, bd), 1.97 (2H, t), 1.87 (2H, d), 3.48 (2H, s), 3.88 (3H, s), 4.07 (2H, dd), 6.92 (1H, t), 7.03~7.10 (2H, m), 7.18~7.29 (3H, m), 7.46 (1H, d)

MS: (M+1$^+$)=413 (FAB)

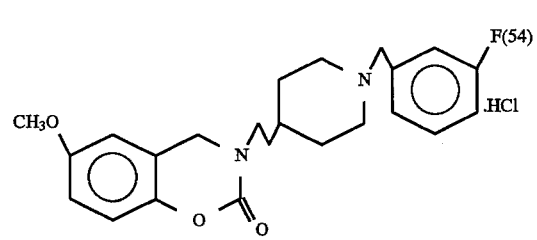

(54)

Melting point: 229°~230° C.

Molecular formula: $C_{23}H_{27}N_2O_3F \cdot HCl$

NMR (CDCl$_3$) δ: 1.22~1.39 (3H, m), 1.58~1.65 (2H, m), 1.72 (2H, bd), 1.96 (2H, t), 2.84 (2H, d), 3.46 (2H, s), 3.50 (2H, t), 3.78 (3H, s), 4.41 (2H, s), 6.60 (1H, d), 6.79 (1H, dd), 6.90~6.98 (2H, m), 7.02~7.10 (2H, m), 7.20~7.30 (1H, m)

MS: (M+1$^+$)=399 (FAB)

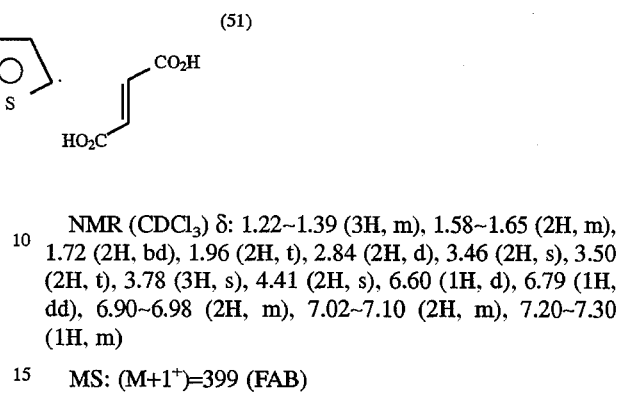

(55)

Melting point: 100°~101° C.

Molecular formula: $C_{20}H_{28}N_2O_5$

NMR (CDCl$_3$) δ: 1.30~1.41 (3H, m), 1.60 (2H, dd), 1.72 (2H, d), 2.06 (2H, t), 2.56 (2H, d), 2.98 (2H, d), 3.49 (2H, dd), 3.78 (3H, s), 3.82~4.00 (4H, m), 4.41 (2H, s), 5.00 (1H, t), 6.60 (1H, d), 6.79 (1H, dd), 6.95 (1H, d)

MS: (M+1$^+$)=377 (FAB)

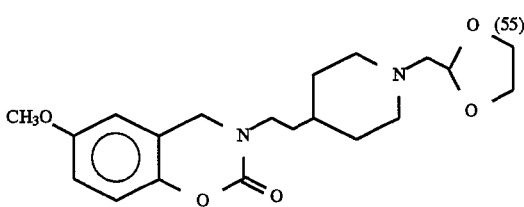

(56)

Melting point: 243°~244° C. (decomp.)

Molecular formula: $C_{21}H_{24}N_2O_2 \cdot HCl$

NMR (CDCl$_3$) δ: 1.24~2.48 (7H, m) 2.72~3.02 (2H, m), 3.32 (2H, d), 3.48 (2H, s), 4.42 (2H, s), 6.68~7.40 (9H, m)

MS: M$^+$=336 (FD)

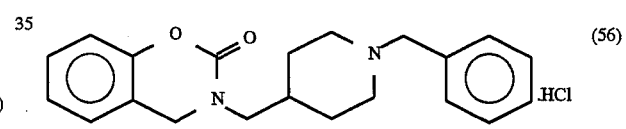

(57)

Melting point: 264°~265° C. (decomp.)

Molecular formula: $C_{21}H_{23}N_2O_2Br \cdot HCl$

NMR (CDCl$_3$) δ: 1.24~2.52 (7H, m), 2.80~3.10 (2H, m), 3.31 (2H, d), 3.64 (2H, s), 4.38 (2H, s), 6.70~7.40 (8H, m)

MS: M$^+$+1=416 (FD) M$^+$–1=414 (FD)

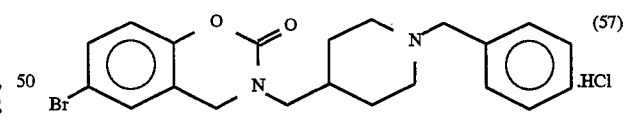

(58)

Melting point: 261°~263° C. (decomp.)

Molecular formula: $C_{21}H_{25}N_3O_2 \cdot HCl$

NMR (CDCl₃) δ: 1.16~2.26 (7H, m), 2.48 (3H, s), 2.76~3.05 (2H, m), 3.32 (2H, d), 3.54 (2H, s), 4.48 (2H, s), 6.92~7.34 (7H, m)

MS: M⁺=351 (FD)

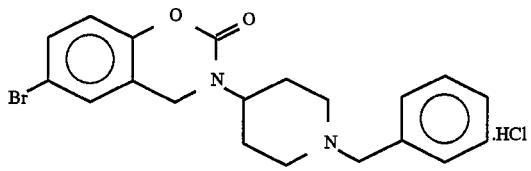
(59)

Melting point: 116°~117° C.

Molecular formula: C₂₀H₂₁N₂O₂Br.HCl

NMR (CDCl₂) δ: 1.58~2.48 (6H, m), 2.84~3.18 (2H, m), 3.51 (2H, s), 4.04~4.30 (1H, m), 4.32 (2H, s), 6.84 (1H, d), 7.14~7.40 (7H, m)

MS: M⁺+1=402 (FD) M⁺−1=400 (FD)

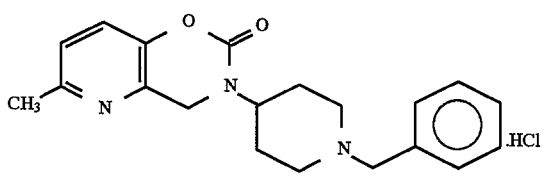
(60)

Melting point: 250°~252° C. (decomp.)

Molecular formula: C₂₀H₂₃N₃O₂.HCl

NMR (CDCl₃) δ: 1.60~2.40 (6H, m), 2.48 (3H, s), 2.84~3.12 (2H, m), 3.52 (2H, s), 4.04~4.32 (1H, m), 4.41 (2H, s), 6.88~7.16 (2H, m), 7.25 (5H, bs)

MS: M⁺=337 (FD)

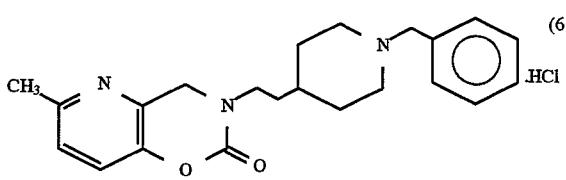
(61)

Melting point: 210°~213° C. (decomp.)

Molecular formula: C₂₂H₂₇N₃O₂.HCl

NMR (CDCl₃) δ: 1.16~2.15 (9H, m), 2.48 (3H, s), 2.70~2.96 (2H, m), 3.45 (2H, s), 3.47 (2H, t), 4.44 (2H, s), 6.80~7.40 (7H, m)

MS: M+1⁺=366 (FAB)

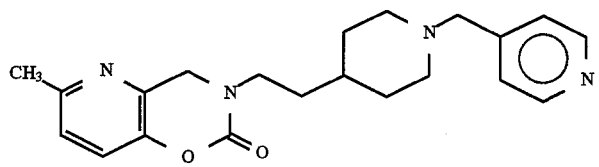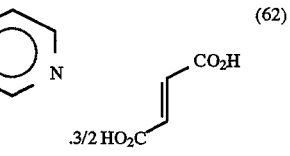
(62)

Melting point: 183°~184° C. (decomp.)

Molecular formula: C₂₁H₂₆N₄O₂.³/₂C₄H₄O₄

NMR (CDCl₃) δ: 1.08~2.20 (9H, m), 2.49 (3H, s), 2.64~2.96 (2H, m), 3.44 (2H, s), 3.50 (2H, t), 4.47 (2H, s), 6.88~7.30 (4H, m), 8.44 (2H, d)

MS: M⁺+1=367 (FAB)

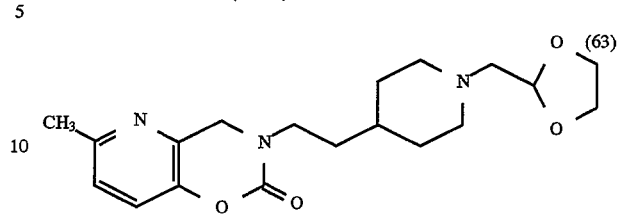
(63)

Melting point: 111° C.

Molecular formula: C₁₉H₂₇N₃O₄

NMR (CDCl₃) δ: 1.27~1.80 (7H, m), 2.08 (2H, t), 2.53 (3H, s), 2.57 (2H, d), 2.99 (2H, d), 3.55 (2H, t), 3.80~4.04 (4H, m), 4.51 (2H, s), 5.00 (1H, t), 7.06 (1H, d), 7.24 (1H, d)

MS: M⁺+1=362 (FAB)

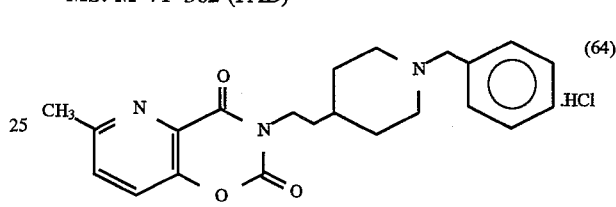
(64)

Melting point: 70° C.

Molecular formula: C₂₂H₂₅N₃O₃.HCl

NMR (CDCl₃) δ: 1.24~1.40 (3H, m), 1.62~1.84 (4H, m), 1.88~2.05 (2H, t), 2.70 (3H, s), 2.87 (2H, d), 3.48 (2H, s), 4.09 (2H, t), 7.20~7.36 (5H, m), 7.48 (1H, d), 7.53 (1H, d)

MS: M⁺+1=380 (FAB)

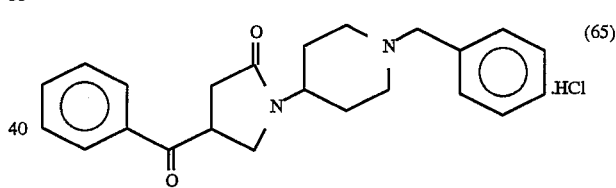
(65)

Melting point: 233°~235° C.

Molecular formula: C₂₃H₂₆N₂O₂.HCl

NMR(CDCl₃) δ: 1.44~2.28 (6H, m), 2.60~3.08 (4H, m), 3.32~4.24 (6H, m), 7.12~7.72 (8H, m), 7.76~8.00 (2H, m)

MS: (M+1⁺)=363 (FAB)

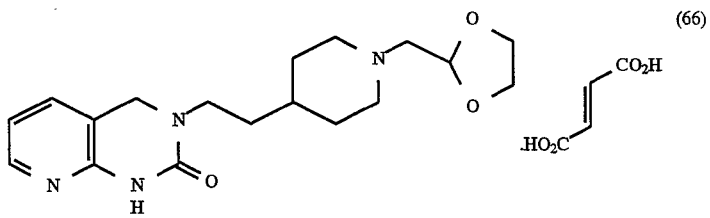
(66)

Melting point: 158°~160° C. (decomp.)

Molecular formula: $C_{18}H_{26}N_4O_3 \cdot C_4H_4O_4$

NMR (CDCl$_3$) δ: 1.20~1.40 (3H, m), 1.47~1.60 (2H, m), 1.65~1.78 (2H, m), 2.00~2.13 (2H, br t), 2.53~2.78 (2H, d), 2.93~3.03 (2H, d), 3.40~3.50 (2H, m), 3.80~4.00 (4H, m), 4.41 (2H, s), 4.98 (1H, t), 6.80~6.87 (1H, dd), 7.31~7.37 (1H, m), 8.20~8.27 (1H, m), 9.08 (1H, s)

MS: (M+1$^+$)=347 (FAB)

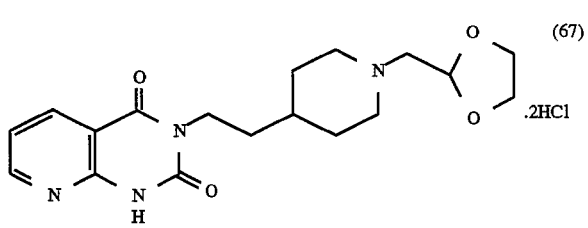
(67)

Melting point: 262°~263° C. (decomp.)

Molecular formula: $C_{18}H_{24}N_4O_4 \cdot 2HCl$

NMR(CDCl$_3$) δ: 1.30~1.45 (2H, m), 1.50~1.85 (5H, m), 2.00~2.15 (2H, br t), 2.52~2.60 (2H, d), 2.95~3.05 (2H, br d), 3.80~4.15 (6H, m), 5.01 (1H, t), 7.20~7.27 (1H, m), 8.42~8.47 (1H, m), 8.70~8.75 (1H, m), 10.96 (1H, br s)

MS: (M+1$^+$)=361 (FAB)

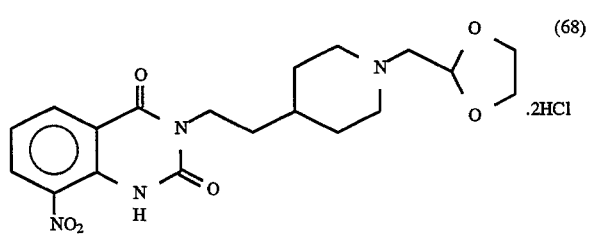
(68)

Melting point: 166°~168° C.

Molecular formula: $C_{18}H_{24}N_4O_6 \cdot HCl$

NMR (CDCl$_3$) δ: 1.25~1.45 (2H, m), 1.50~1.80 (5H, m), 2.00~2.13 (2H, br t), 2.53~2.60 (2H, d), 2.95~3.05 (2H, br d), 3.80~4.15 (6H, m), 5.00 (1H, t), 7.34 (1H, t), 8.50~8.55 (1H, dd), 8.55~8.60 (1H, dd), 10.43 (1H, br s)

MS: (M+1$^+$)=405 (FAB)

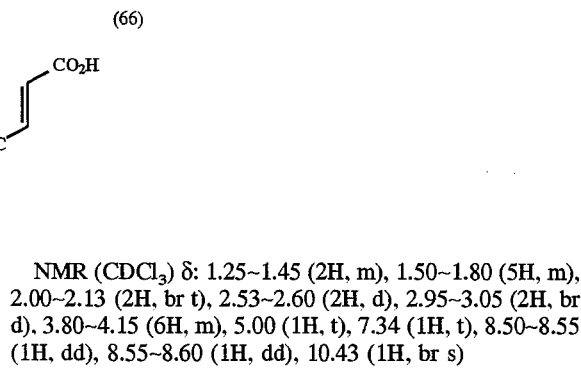
(69)

Melting point: 235°~238° C. (decomp.)

Molecular formula: $C_{21}H_{22}F_2N_4O_2 \cdot 2HCl$

NMR (CDCl$_3$/CD$_3$OD) δ: 1.08~2.24 (9H, m), 2.64~3.04 (2H, m), 3.48 (2H, s), 3.92~4.24 (2H, m), 6.52~7.00 (3H, m), 7.12~7.40 (1H, dd), 8.32~8.52 (1H, dd), 8.56~8.72 (1H, dd)

MS: (M+1$^+$)=401 (FAB)

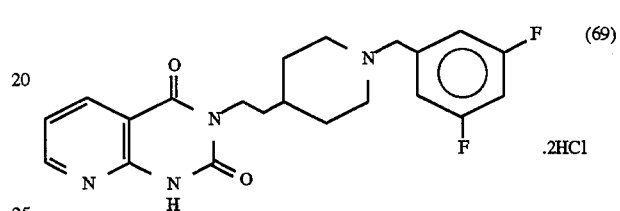
(70)

Melting point: 245°~247° C. (decomp.)

Molecular formula: $C_{23}H_{26}N_4O_2 \cdot 2HCl$

NMR (CDCl$_3$) δ: 1.08~2.24 (9H, m), 2.76~3.28 (4H, m), 3.80~4.20 (2H, m), 6.04~6.64 (2H, m), 7.00~7.40 (6H, m), 8.24~8.48 (1H, dd), 8.56~8.76 (1H, dd)

MS: (M+1$^+$)=391 (FAB)

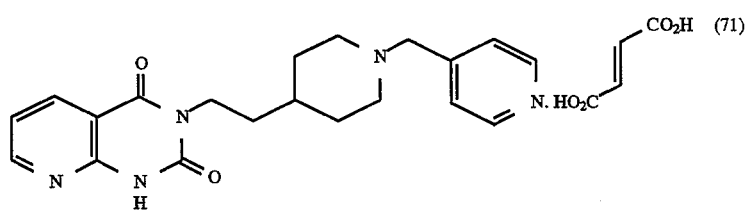
(71)

Melting point: 182°~184° C.
Molecular formula: $C_{20}H_{23}N_5O_2 \cdot C_4H_4O_4$
NMR (CDCl$_3$) δ: 1.08~2.28 (9H, m), 2.64~3.00 (2H, m), 3.44 (2H, s), 3.84~4.20 (2H, m), 7.00~7.36 (3H, m), 8.24~8.80 (4H, m)
MS: (M+1$^+$)=366 (FAB)

(72)

Melting point: 220° C. (decomp.)
Molecular formula: $C_{21}H_{23}FN_4O_2 \cdot 2HCl$
NMR (CDCl$_3$) δ: 1.04~2.24 (9H, m), 2.68~3.04 (2H, m), 3.44 (2H, s), 3.88~4.24 (2H, m), 6.76~7.36 (5H, m), 8.28~8.48 (1H, dd), 8.60~8.76 (1H, dd)
MS: (M+1$^+$)=383 (FAB)

(73)

Melting point: 220°~222° C. (decomp.)
Molecular formula: $C_{21}H_{24}N_4O_2 \cdot 2HCl$
NMR (CDCl$_3$) δ: 1.00~2.20 (9H, m), 2.60~3.00 (2H, m), 3.44 (2H, s), 3.88~4.20 (2H, m), 7.08~7.36 (6H, m), 8.28~8.48 (1H, dd), 8.60~8.76 (1H, dd)
MS: (M+1$^+$)=365 (FAB)

(74)

Melting Point: amorphous
Molecular formula: $C_{27}H_{34}N_2O_3 \cdot HCl$
NMR (CDCl$_3$) δ: 1.04~2.20 (12H, m), 2.56~3.00 (4H, m), 3.12~3.80 (6H, m), 3.88~4.32 (3H, m), 6.72~7.72 (9H, m)
MS: M$^+$=434 (FD)

(75)

Melting point: amorphous
Molecular formula: $C_{27}H_{34}N_2O_3 \cdot HCl$
NMR (CDCl$_3$) δ: 1.00~2.40 (12H, m), 2.48~3.04 (4H, m), 3.08~4.28 (9H, m), 6.80~7.00 (2H, d), 7.08~7.36 (5H, m), 7.72~7.96 (2H, d)
MS: M$^+$=434 (FD)

Example 76

(76)

Mol. Form. $C_{21}H_{28}N_2O_5 \cdot C_4H_4O_4$

NMR (δ, solv. CDCl$_3$) 1.30~1.60 (7H, m), 1.61~1.68 (2H, m), 1.75~1.79 (2H, m), 1.82~2.09 (2H, m), 1.94~2.08 (3H, m), 2.41~2.52 (2H, m), 2.99~3.06 (2H, m), 3.87 (3H, s), 4.03~4.08 (2H, m), 7.19 (1H, d, J=9.0 Hz), 7.25 (1H, dd, J=3.0 Hz, 9.0 Hz), 7.45 (1H, d, J=3.0 Hz)

MS (determn. method) M$^+$=389 (FAB) (M+1$^+$)

M.P. (°C.) 138.8°~139.2° C.

(77)

Mol. Form. $C_{21}H_{30}N_2O_4 \cdot C_4H_4O_4$

NMR (δ, solv. CDCl$_3$) 1.30~2.10 (13H, m), 2.18~2.51 (2H, m), 3.01 (2H, bt), 3.49 (2H, m), 3.70~3.68 (1H, m), 3.77 (3H, s), 3.82~3.88 (1H, m), 4.01~4.08 (1H, m), 4.41 (2H, s), 6.64~6.84 (2H, m), 6.94~6.96 (1H, m)

MS (determn. method) M⁺=375 (FAB) (M+1⁺)

M.P. (°C.) 152.5°~152.8° C.

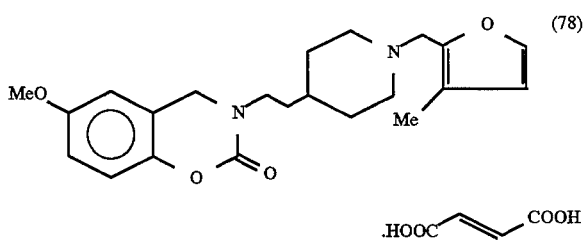

Mol. Form. C₂₂H₂₈N₂O₄

NMR (δ, solv. CDCl₃) 1.31~1.38 (3H, m), 1.58~1.65 (4H, m), 1.86~2.00 (2H, m), 2.01 (3H, s), 2.88 (2H, bd), 3.46 (2H, s), 3.50 (2H, bt), 3.78 (3H, s), 4.40 (2H, s), 6.60 (1H, d, J=2.8 Hz), 6.72 (1H, d, J=1.4 Hz), 6.79 (1H, dd, J=2.8 Hz, 9.0 Hz), 6.95 (1H, d, J=9.0 Hz), 7.28 (1H, d, J=1.4 Hz)

MS (determn. method) M⁺=385 (FAB) (M+1⁺)

M.P. (°C.) 171.8~172.2° C.

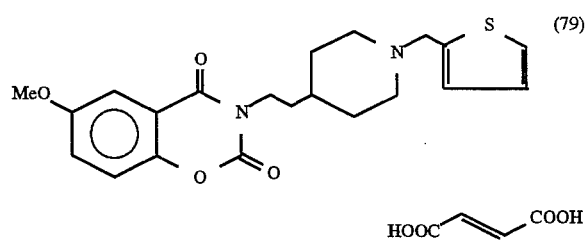

Mol. Form. C₂₁H₂₄N₂O₄S.C₄H₄O₄

NMR (δ, solv. CDCl₃) 1.32~1.38 (3H, m), 1.62~1.66 (2H, m), 1.75~1.79 (2H, m), 1.99 (2H, bt), 2.92 (2H, bd), 3.71 (2H, s), 3.87 (3H, s), 4.02~4.05 (2H, m), 6.88~6.90 (1H, m), 7.18~7.26 (4H, m), 7.43~7.46 (1H, m)

MS (determn. method) M⁺=401 (FAB) (M+1⁺)

M.P. (°C.) 190.2°~190.8° C.

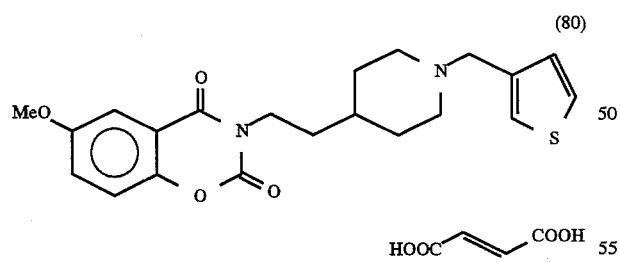

Mol. Form. C₂₁H₂₄N₂O₄S.C₄H₄O₄

NMR (δ, solv. CDCl₃) 1.33~1.38 (3H, m), 1.62~1.67 (2H, m), 1.75~1.78 (2H, m), 1.95 (2H, bt), 2.89 (2H, bd), 3.52 (2H, s), 3.87 (3H, s), 4.04~4.07 (2H, m), 7.05 (1H, d, J=4.8 Hz), 7.10 (1H, bs), 7.19 (1H, d, J=8.8 Hz), 7.23~7.27 (2H, m), 7.45 (1H, d, J=2.8 Hz)

MS (determn. method) M⁺=401 (FAB) (M+1⁺)

M.P. (°C.) 197.2°~198.0° C.

Example 81

{(N-Benzyl-N-methyl)-5-aminopentyl}-6-methoxy-2H-3,4-dihydro-1,3-benzoxazin-2-one fumarate

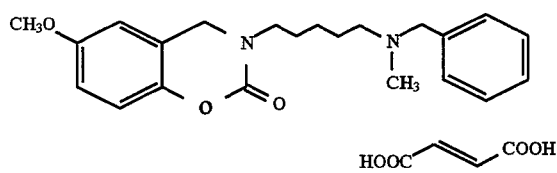

10 ml of methanol was added to 1.62 g of N-benzyl-N-methyl-1,5-diaminopentane to prepare a solution, which was stirred at room temperature. 0.98 ml of 5-methoxysalicylaldehyde was added to the solution and the solution was stirred as such for 20 min. The reaction mixture was cooled with ice and sodium borohydride was added in small portions thereto until the reaction liquid turned pale yellow. After stirring at room temperature for additional 30 min, the solvent was distilled off. A saturated aqueous solution of sodium hydrogencarbonate and ethyl acetate were added thereto and the solution was thoroughly stirred. An organic layer thus formed was separated. The aqueous layer was extracted with ethyl acetate. The organic layer and the extract were combined together and washed with a saturated aqueous solution of common salt. After drying over magnesium sulfate, the solvent was distilled off. 30 ml of tetrahydrofuran was added to the residue to prepare a solution. 1.91 g of N,N-carbonyldiimidazole was added to the solution and the resulting solution was heated under reflux for 3 h. The solvent was distilled off. An oily product thus obtained was purified by silica gel column chromatography to give 1.44 g of a colorless oily product, which was dissolved in methanol. A solution of 0.45 g of fumaric acid in methanol was added thereto. The solvent was distilled off to give 1.89 g of the title compound in the form of a colorless amorphous substance.

Mol. Form. C₂₂H₂₈N₂O₃.C₄H₄O₄

NMR (δ, solv. CDCl₃) 1.33~1.41 (2H, m), 1.52~1.70 (4H, m), 2.18 (3H, s), 2.36 (2H, t, J=7.4 Hz), 3.45 (2H, t, J=7.6 Hz), 3.47 (2H, s), 3.78 (3H, s), 4.41 (2H, s), 6.59 (1H, d, J=2.8 Hz), 6.80 (1H, dd, J=2.8 Hz, 8.8 Hz), 6.96 (1H, d, J=8.8 Hz), 7.21~7.30 (5H, m)

MS (determn. method) M⁺=369 (FAB) (M+1⁺)

M.P. (°C.) amorphous

Example 82

{(N-Benzyl-N-methyl)-5-aminopentyl}-6-methoxy-2H-3,4-dihydro-1,3-benzoxazine-2,4-dione fumarate

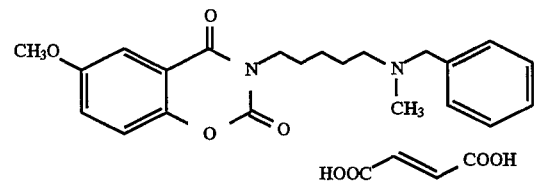

10 ml of tetrahydrofuran was added to 1.57 g of 2-methoxymethyl-5-methoxybenzoic acid to prepare a solution. 1.91 g of N,N-carbonyldiimidazole was added to the solution and the resulting solution was stirred at room temperature for 15 min. A solution of 1.43 g of N-benzyl-N-methyl-1,5-diaminopentane in 5 ml of tetrahydrofuran was added thereto. After stirring for additional 13 h, the solvent was distilled off. The residue was cooled With ice and 8.3 ml of 5N hydrochloric acid and 5 ml of methanol were added thereto. The resulting solution was stirred at room temperature for 4.5 h. Methanol was distilled off under reduced pressure and the residue was cooled with ice. The pH of the reaction mixture was adjusted to 8 with sodium hydrogencarbonate. After extraction with ethyl acetate twice followed by washing with a saturated aqueous common salt solution and drying over magnesium sulfate, the solvent was distilled off. 30 ml of tetrahydrofuran was added thereto to prepare a solution. 2.24 g of N,N-carbonyldiimidazole was added to the solution and the resulting solution was heated under reflux for 16 hr. The solvent was distilled off. An oily product thus obtained was purified by silica gel column chromatography to give 2.16 g of a colorless oily product, which was dissolved in methanol. A solution of 0.66 g of fumaric acid in methanol was added to the solution. The solvent was distilled off to give 2.82 g of the title compound in the form of colorless amorphous substance.

Mol. Form. $C_{22}H_{26}N_2O_4 \cdot C_4H_4O_4$

NMR (δ, solv. CDCl$_3$) 1.40 (2H, broad quintet), 1.57 (2H, broad quintet), 1.72 (2H, broad quintet), 2.17 (3H, s), 2.37 (2H, t, J=7.2 Hz), 3.47 (2H, s), 3.87 (3H, s), 4.03 (2H, t, J=7.6 Hz), 7.18~7.44 (8H, m)

MS (determn. method) M$^+$=383 (FAB) (M+1$^+$)

M.P. (°C.) amorphous

Examples 83 to 87

Compounds listed below were produced in the same manner as that of Examples 81 and 82.

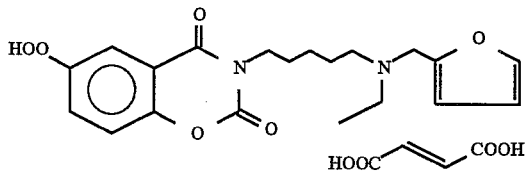
(83)

Mol. Form. $C_{18}H_{26}N_2O_5 \cdot C_4H_4O_4$

NMR (δ, solv. CDCl$_3$) 1.49~1.74 (4H, m), 2.32 (3H, s), 2.48 (2H, t, J=7.2 Hz), 2.57 (2H, d, J=4.5 Hz), 3.48 (2H, t, J=7.6 Hz), 3.78 (3H, s), 3.81~3.84 (2H, m), 3.86~3.89 (2H, m), 4.43 (2H, s), 4.95 (1H, t, J=4.5 Hz), 6.59 (1H, d, J=3.2 Hz), 6.79 (1H, dd, J=3.2 Hz, 8.8 Hz), 6.96 (1H, d, J=8.8 Hz)

MS (determn. method) M$^+$=351 (FAB) (M+1$^+$)

M.P. (°C.) amorphous

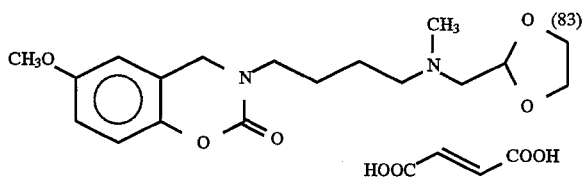
(84)

Mol. Form. $C_{21}H_{26}N_2O_2 \cdot C_4H_4O_4$

NMR (δ, solv. CDCl$_3$) 1.03 (3H, t, J=7.2 Hz), 1.51 (2H, quintet, J=7.6 Hz), 1.66 (2H, quintet, J=7.6 Hz), 2.46 (2H, t, J=7.2 Hz), 2.50 (2H, q, J=7.5 Hz), 3.42 (2H, t, J=7.6 Hz), 3.54 (2H, s), 4.39 (2H, s), 6.99~7.11 (4H, m), 7.19~7.32 (5H, m)

MS (determn. method) M$^+$=339 (FAB) (M+1$^+$)

M.P. (°C.) amorphous (85)

Mol. Form. $C_{21}H_{26}N_2O_5 \cdot C_4H_4O_4$

NMR (δ, solv. CDCl$_3$) 1.06 (3H, t, J=7.2 Hz), 1.37 (2H, quintet, J=7.2 Hz), 1.45~1.58 (2H, m), 1.72 (2H, quintet, J=7.5 Hz), 2.43 (2H, t, J=7.6 Hz), 2.51 (2H, q, J=7.2 Hz), 3.64 (2H, s), 3.87 (3H, s), 4.03 (2H, t, J=7.5 Hz), 6.15 (1H, d, J=3.0 Hz), 6.30 (1H, dd, J=3.2 Hz, 2.0 Hz), 7.20 (1H, d, J=8.8 Hz), 7.25 (1H, dd, J=3.0 Hz, 8.8 Hz), 7.34~7.36 (1H, m), 7.46 (1H, d, J=3.2 Hz)

MS (determn. method) M$^+$=387 (FAB) (M+1$^+$) (M+1$^-$)

M.P. (°C.) amorphous (86)

Mol. Form. $C_{21}H_{27}ClN_2O_2S \cdot C_4H_4)_4$

NMR (δ, solv. CDCl$_3$) 1.05 (3H, t, J=7.1 Hz), 1.33~1.38 (4H, m), 1.45~1.53 (2H, m), 1.62~1.70 (2H, m), 2.43 (2H, t, J=7.4 Hz), 2.53 (2H, q, J=7.1 Hz), 3.45 (2H, t, J=7.6 Hz), 3.79 (2H, s), 4.42 (2H, s), 6.80~6.90 (3H, m), 7.07~7.10 (1H, m), 7.18~7.24 (2H, m)

MS (determn. method) M$^+$=407 (FAB) (M+1$^+$)

M.P. (°C.) amorphous (87)

Mol. Form. $C_{20}H_{24}ClN_3O_3 \cdot C_4H_4O_4$

NMR (δ, solv. CDCl$_3$) 1.05 (3H, t, J=7.2 Hz), 1.39 (2H, broad quintet), 1.56 (2H, broad quintet), 1.72 (2H, broad quintet), 2.44 (2H, t, J=7.2 Hz), 2.51 (2H, q, J=7.2 Hz), 3.64 (2H, s), 4.06 (2H, t, J=7.6 Hz), 6.15 (1H, d, J=3.4 Hz), 6.29 (1H, dd, J=2.0 Hz, 3.4 Hz); 7.05 (1H, d, J=8.8 Hz), 7.35 (1H, dd, J=0.8 Hz, 2.0 Hz), 7.54 (1H, dd, J=2.4 Hz, 8.8 Hz), 8.10 (1H, d, J=2.4 Hz)

MS (determn. method) M$^+$=390 (FAB) (M+1$^+$)

M.P. (°C.) amorphous

We claim:

1. A cyclic amide derivative having the formula or a pharmacologically acceptable salt thereof $R^1$—(CH$_2$)$_n$—Z wherein R$^1$ is

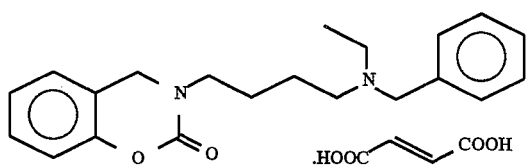

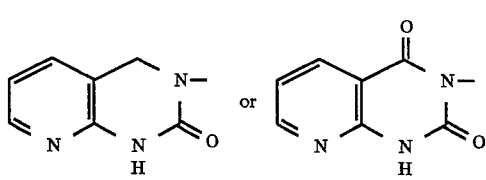

substituted or unsubstituted, n is zero or an integer of 1 to 10 and Z is

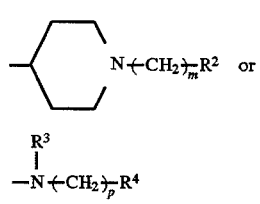

R² is an aryl, a substituted aryl, a cycloalkyl or a heterocyclic group, m is an integer of 1 to 6, R³ is hydrogen or a lower alkyl, R⁴ is an aryl or a substituted aryl, a cycloalkyl or a heterocyclic group, p is an integer of 1 to 6.

2. The cyclic amide derivative as claimed in claim 1 or a pharmacologically acceptable salt thereof wherein Z is (1).

3. The cyclic amide derivative as claimed in claim 1 or a pharmacologically acceptable salt thereof wherein Z is (1) and R² is selected from the group consisting of phenyl, pyridyl, cyclopentyl and 1,3-dioxane-2-yl, n is 1 or 2 and m is 1 or 2.

4. The cyclic amide derivative as claimed in claim 1 or a pharmacologically acceptable salt thereof wherein Z is (1), R² is selected from the group consisting of phenyl, pyridyl, cyclopentyl and 1,3-dioxane-2-yl, n is 1 or 2, m is 1 or 2.

5. The cyclic amide derivative as claimed in claim 4 or a pharmacologically acceptable salt thereof wherein R¹ is substituted with a lower alkyl or a lower alkoxy.

6. The cyclic amide derivative as claimed in claim 4 or a pharmacologically acceptable salt thereof wherein R¹ is substituted with methoxy.

7. The cyclic amide derivative as claimed in claim 1 or a pharmacologically acceptable salt thereof wherein Z is (2).

8. The cyclic amide derivative as claimed in claim 1 or a pharmacologically acceptable salt thereof wherein Z is (2), R³ is a lower alkyl and R⁴ is selected from phenyl, pyridyl, cyclopentyl and 1,3-dioxane-2-yl.

9. The compound according to claim 1 which has the formula

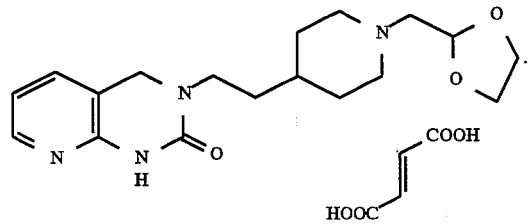

10. The compound according to claim 1 which has the formula

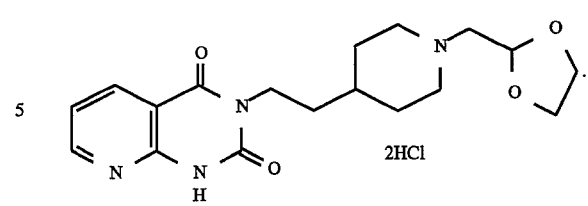

11. The compound according to claim 1 which has the formula

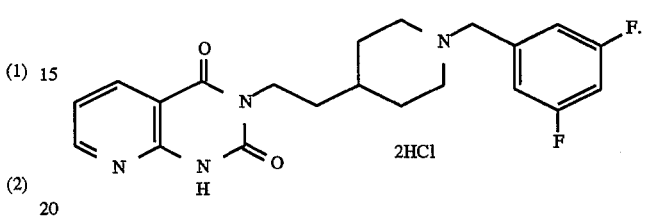

12. The compound according to claim 1 which has the formula

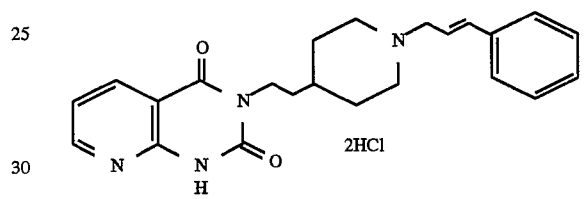

13. The compound according to claim 1 which has the formula

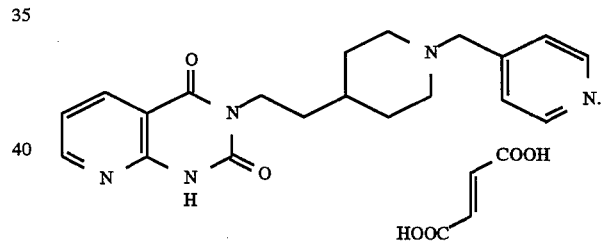

14. The compound according to claim 1 which has the formula

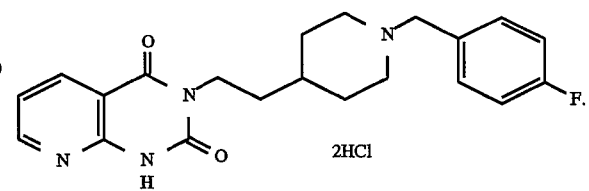

15. The compound according to claim 1 which has the formula

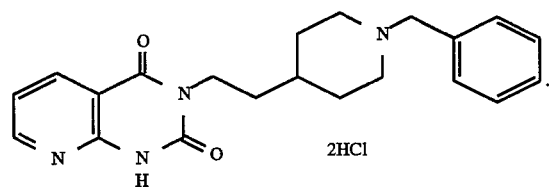

16. A pharmaceutical composition comprising a pharmacologically effective amount of the cyclic amide derivative as defined in claim 1 and a pharmacologically acceptable carrier.

17. A method for treating diseases due to insufficiency of the central choline functions by administering a pharmacologically effective amount of the cyclic amide derivative as defined in claim 1 to a human patient suffering from the diseases.

* * * * *